(12) United States Patent
Puleo et al.

(10) Patent No.: US 12,201,836 B2
(45) Date of Patent: *Jan. 21, 2025

(54) TECHNIQUES FOR NEUROMODULATION

(71) Applicant: General Electric Company, Schenectady, NY (US)

(72) Inventors: Christopher Michael Puleo, Niskayuna, NY (US); Jeffrey Michael Ashe, Gloversville, NY (US); Victoria Eugenia Cotero, Watervliet, NY (US); Michael Ernest Marino, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 579 days.

This patent is subject to a terminal disclaimer.

(21) Appl. No.: 17/342,186

(22) Filed: Jun. 8, 2021

(65) Prior Publication Data

US 2021/0299449 A1 Sep. 30, 2021

Related U.S. Application Data

(63) Continuation of application No. 16/091,486, filed as application No. PCT/US2017/025971 on Apr. 4, 2017, now Pat. No. 11,040,199.

(60) Provisional application No. 62/325,828, filed on Apr. 21, 2016, provisional application No. 62/318,035, filed on Apr. 4, 2016.

(51) Int. Cl.
*A61N 1/36* (2006.01)
*A61N 2/00* (2006.01)

(52) U.S. Cl.
CPC ....... *A61N 1/36071* (2013.01); *A61N 1/3606* (2013.01); *A61N 1/36121* (2013.01); *A61N 1/36153* (2013.01); *A61N 1/36171* (2013.01); *A61N 2/006* (2013.01)

(58) Field of Classification Search
CPC .............. A61N 1/3606; A61N 1/36071; A61N 1/36121; A61N 1/36153; A61N 1/36171; A61N 2/006
See application file for complete search history.

(56) References Cited

U.S. PATENT DOCUMENTS

| 5,305,745 A | 4/1994 | Zacouto |
| 5,391,143 A | 2/1995 | Kensey |

(Continued)

FOREIGN PATENT DOCUMENTS

| WO | 2006007048 A2 | 1/2006 |

OTHER PUBLICATIONS

Giglioiti. el al 'Ultrasound Prevents Renal Ischemia,Reperfusion Injury By Stimulating the Splenic Cholinergic Anti-Inflammatory Pathway'. Jasn. Sep. 2013, Z,T, pp. 1340-1342, Published Ahead of Print Aug. 1, 2013, ISSN 1046-6673.

(Continued)

*Primary Examiner* — Christopher A Flory
(74) *Attorney, Agent, or Firm* — Fletcher Yoder, P.C.

(57) ABSTRACT

The subject matter of the present disclosure generally relates to techniques for neuromodulation of lymphatic tissue that include applying one or more energy pulses to a neuron of a subject, e.g., via an electrode positioned to deliver sufficient energy to the neuron, to modulate immune function. For example, an adaptive immune reflex of a subject may be modulated via neuromodulation.

15 Claims, 34 Drawing Sheets

(56) References Cited

U.S. PATENT DOCUMENTS

| | | | |
|---|---|---|---|
| 6,038,478 A | 3/2000 | Yuen et al. | |
| 6,115,637 A | 9/2000 | Lennox et al. | |
| 6,721,603 B2 | 4/2004 | Zabara et al. | |
| 6,901,296 B1 | 5/2005 | Whitehurst et al. | |
| 6,970,741 B1 | 11/2005 | Whitehurst et al. | |
| 7,418,292 B2 | 8/2008 | Shafer | |
| 7,526,337 B2 | 4/2009 | Shuros et al. | |
| 7,894,906 B2 | 2/2011 | Shuros | |
| 7,904,162 B2 | 3/2011 | Whitehurst et al. | |
| 8,321,012 B2 | 11/2012 | Della Rocca et al. | |
| 9,108,057 B2 | 8/2015 | Rezai et al. | |
| 9,211,409 B2 | 12/2015 | Tracey et al. | |
| 2003/0036773 A1 | 2/2003 | Whitehurst et al. | |
| 2003/0113303 A1 | 6/2003 | Schwartz | |
| 2004/0158297 A1 | 8/2004 | Gonzalez | |
| 2005/0075701 A1 | 4/2005 | Shafer | |
| 2005/0075702 A1 | 4/2005 | Shafer | |
| 2005/0143787 A1 | 6/2005 | Boveja et al. | |
| 2006/0111754 A1 | 5/2006 | Rezai et al. | |
| 2007/0027484 A1 | 2/2007 | Guzman et al. | |
| 2007/0049514 A1 | 3/2007 | Morgan | |
| 2007/0156179 A1 | 7/2007 | S.E. | |
| 2007/0244520 A1 | 10/2007 | Ferren et al. | |
| 2007/0282376 A1 | 12/2007 | Shuros et al. | |
| 2007/0282380 A1 | 12/2007 | Brooke et al. | |
| 2007/0282382 A1 | 12/2007 | Shuros et al. | |
| 2007/0282386 A1 | 12/2007 | Shuros | |
| 2007/0282390 A1 | 12/2007 | Shuros | |
| 2008/0009719 A1 | 1/2008 | Shuros et al. | |
| 2008/0021503 A1 | 1/2008 | Whitehurst et al. | |
| 2008/0097412 A1 | 4/2008 | Shuros et al. | |
| 2008/0215101 A1 | 9/2008 | Rezai et al. | |
| 2008/0294228 A1 | 11/2008 | Brooke et al. | |
| 2009/0247934 A1 | 10/2009 | Tracey et al. | |
| 2010/0042170 A1 | 2/2010 | Shuros et al. | |
| 2010/0228310 A1 | 9/2010 | Shuros et al. | |
| 2010/0256700 A1 | 10/2010 | Shuros et al. | |
| 2011/0028859 A1 | 2/2011 | Chian | |
| 2011/0029037 A1 | 2/2011 | Rezai et al. | |
| 2011/0150924 A1 | 6/2011 | Della Rocca et al. | |
| 2011/0152967 A1 | 6/2011 | Simon et al. | |
| 2011/0152974 A1 | 6/2011 | Rezai et al. | |
| 2011/0178441 A1* | 7/2011 | Tyler | A61B 5/369 601/2 |
| 2012/0310140 A1 | 12/2012 | Kramer et al. | |
| 2013/0178829 A1 | 7/2013 | Rezai et al. | |
| 2013/0324892 A1 | 12/2013 | Zhu et al. | |
| 2015/0025422 A1 | 1/2015 | Tyler | |
| 2015/0080926 A1* | 3/2015 | Emery | A61N 7/02 606/169 |
| 2015/0111918 A1 | 4/2015 | Sobotka et al. | |
| 2015/0224348 A1 | 8/2015 | Iyer et al. | |
| 2016/0022976 A1* | 1/2016 | Peyman | A61K 47/6929 600/407 |
| 2016/0067491 A1 | 3/2016 | Rezai et al. | |
| 2016/0096016 A1 | 4/2016 | Tracey et al. | |
| 2016/0279021 A1 | 9/2016 | Hyde et al. | |
| 2019/0038898 A1 | 2/2019 | Chavan et al. | |

OTHER PUBLICATIONS

International Search Report and Written Opinion for corresponding PCT application No. PCT/US2017/025971 with a mail date of Jun. 22, 2017; 11 pages.

Rosas-Ballina et al., The Neurology of the Immune System: Neural Reflexes Regulate Immunity, Neuron, Oct. 15, 2009, vol. 64, Issue: 1, pp. 28-32.

Schroeppel et al., Direct current ablation destroys multi-stage fibrosarcomas in rats, 2009 Annual International Conference of the IEEE Engineering in Medicine and Biology Society, Sep. 3-6, 2009, pp. 3099-3104, Conference Location: Minneapolis, MN.

Straub et al., Neuronally released sympathetic neurotransmitters stimulate splenic interferon-γ secretion from T cells in early type II collagen-induced arthritis, Arthritis & Rheumatism, Nov. 2008, vol. 58, Issue: 11, pp. 3450-3460.

Ugalde et al., Model-based design of control modules for neuromodulation devices, 2015 7th International IEEE/EMBS Conference on Neural Engineering (NER), Apr. 22-24, 2015, pp. 462-465 Conference Location: Montpellier.

Chinese Office Action for CN Application No. 201780020897.6 mailed Dec. 3, 2021, 11 pgs.

* cited by examiner

STIMULATION SITE

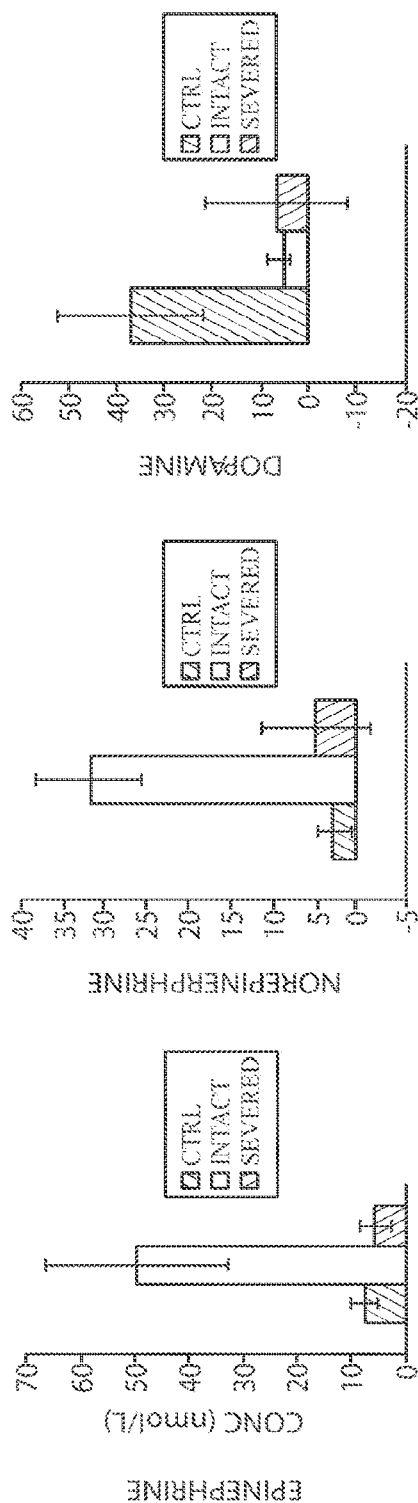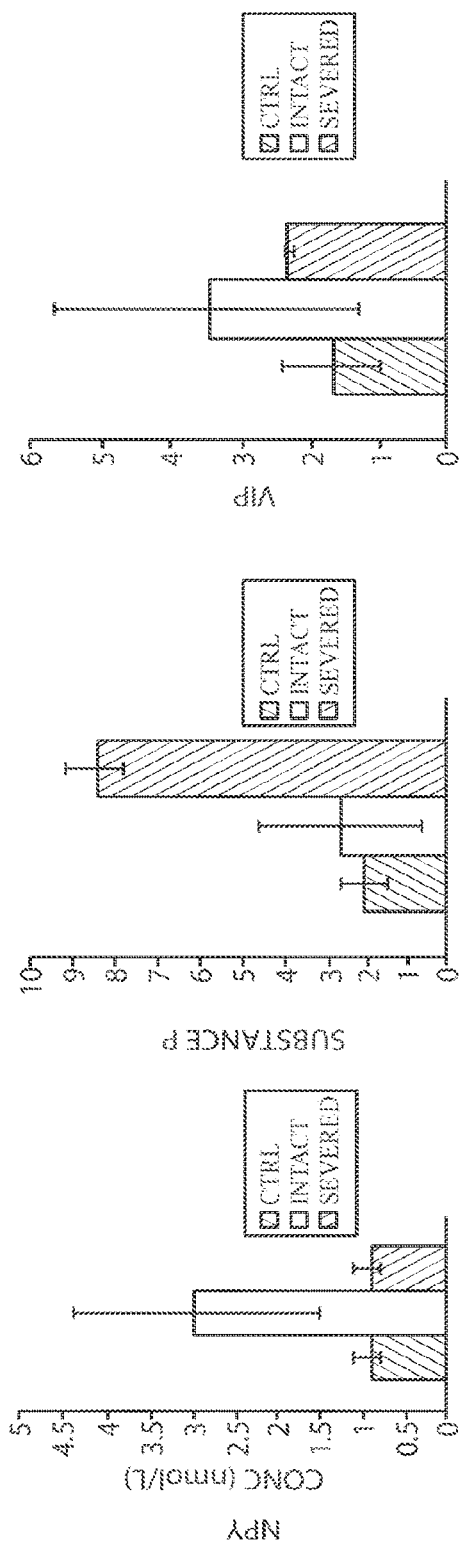

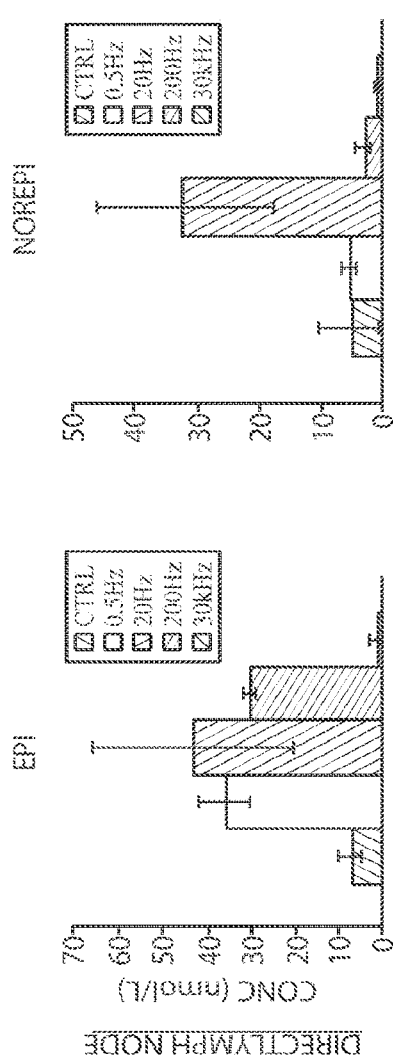
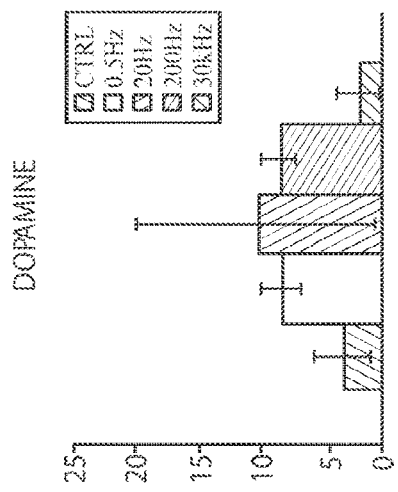
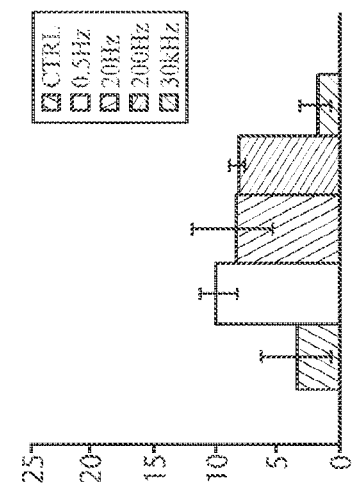
FIG. 24A  FIG. 24B  FIG. 24C
FIG. 24D  FIG. 24E  FIG. 24F

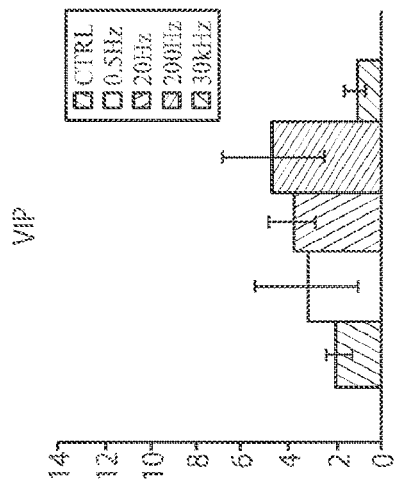
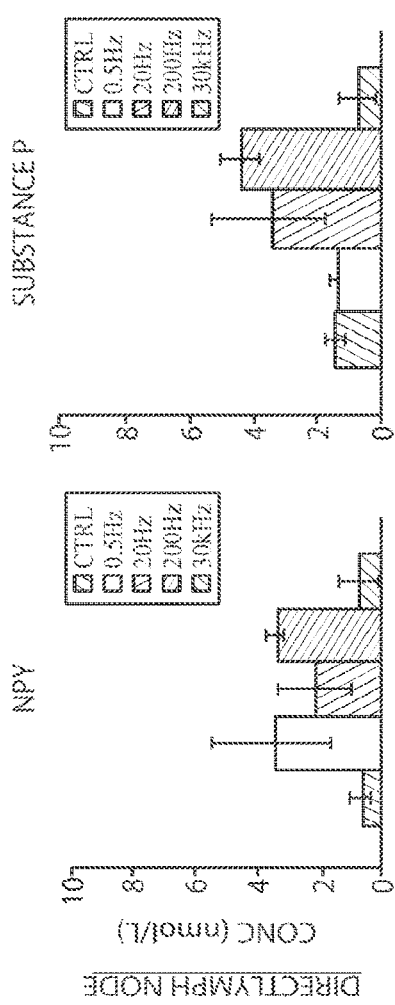
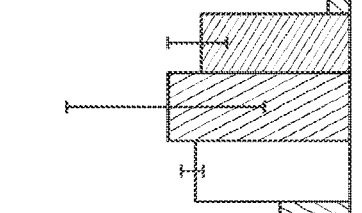
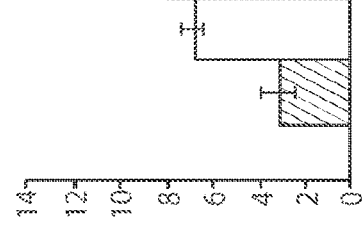
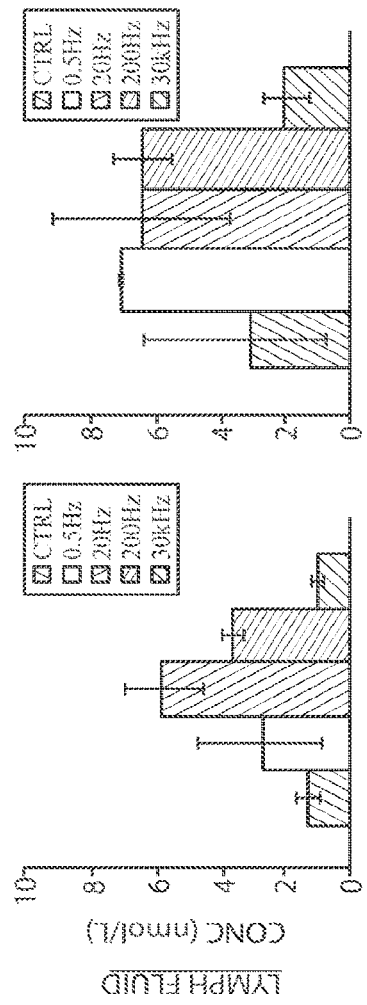

TECHNIQUES FOR NEUROMODULATION

CROSS-REFERENCE TO RELATED APPLICATIONS

This application is a continuation of U.S. patent application Ser. No. 16/091,486, entitled "TECHNIQUES FOR NEUROMODULATION OF LYMPHATIC TISSUE," filed Apr. 4, 2017, which is a 35 U.S.C. 371 filing of international application number PCT/US2017/025971, filed Apr. 4, 2017, which claims priority to U.S. Provisional Patent Application No. 62/318,035, entitled "TECHNIQUES FOR NEUROMODULATION OF LYMPHATIC TISSUE," filed Apr. 4, 2016, and of U.S. Provisional Patent Application No. 62/325,828, entitled "TECHNIQUES FOR NEUROMODULATION OF LYMPHATIC TISSUE," filed Apr. 21, 2016, the disclosures of all of which are herein incorporated in their entirety by reference.

BACKGROUND

The subject matter disclosed herein generally relates to neuromodulation of lymphatic and immune-associated tissue, and specifically, to techniques for differentially stimulating or modulating a physiological response in response to the neuromodulation and, in particular embodiments, using this response to assess the effectiveness of the neuromodulation.

Neuromodulation has been used to treat a variety of clinical conditions. For example, electrical stimulation at various locations along the spinal cord has been used to treat chronic back pain. Such treatment may be performed by an implantable device that periodically generates electrical energy that is applied to the tissue to activate certain nerve fibers, which in turn may result in a decreased sensation of pain. In the case of spinal cord stimulation, the stimulating electrodes are generally positioned in the epidural space, although the pulse generator may be positioned somewhat remotely from the electrodes, e.g., in the abdominal or gluteal region, but connected to the electrodes via conducting wires. In other implementations, deep brain stimulation may be used to stimulate particular areas of the brain to treat movement disorders, and the stimulation locations may be guided by neuroimaging. Such central nervous system stimulation is generally targeted to the local nerve or brain cell function.

Peripheral neuromodulation can be relatively more challenging than targeting the larger structures of the central nervous system. As peripheral nerves extend outward, the size of the nerve bundle decreases. In addition, a small peripheral nerve fiber may control a comparatively large section of surrounding tissue, which makes locating and targeting such nerves for neuromodulation relatively challenging. However, the peripheral nervous system innervates many different organ structures within the body, and targeting certain peripheral nerves may be desirable.

BRIEF DESCRIPTION

In one embodiment, a method of neuromodulation is provided that includes applying one or more energy pulses to a neuron of a subject, e.g., via an electrode positioned to deliver sufficient energy to the neuron, to modulate an adaptive immune system neurological reflex, in which neuromodulation results in a concerted immune response across a portion of the immune/lymphatic system.

In the exemplary embodiment, a method of neuromodulation is provided that includes applying one or more energy pulses to a neuron of a subject via an electrode positioned to deliver sufficient energy to the neuron to stimulate an adaptive immune system neurological reflex, in which immune cell migration or flux through local lymph structures are differentially modulated in a concerted fashion across the lymphatic system.

In another embodiment, a method of neuromodulation is provided that includes applying one or more energy pulses to a neuron of a subject via an electrode positioned to deliver sufficient energy to the neuron to modulate an adaptive immune system neurological reflex, in which immune cell fate and/or phenotype within local lymph structures are differentially modulated in a concerted fashion across the lymphatic system.

In another embodiment, a method of neuromodulation is provided that includes applying one or more energy pulses to a neuron of a subject via an electrode positioned to deliver sufficient energy to the neuron to modulate an adaptive immune system neurological reflex, in which the cytokine secretion profile of immune cells within or exiting local lymph structures are differentially modulated in a concerted fashion across the lymphatic system.

In another embodiment, a method of neuromodulation is provided that includes applying one or more energy pulses to a neuron of a subject via an electrode positioned to deliver sufficient energy to the neuron to modulate an adaptive immune system neurological reflex, in which check point molecule expression of immune cells within or exiting local lymph structures are differentially modulated in a concerted fashion across the lymphatic system.

In exemplary embodiments, modulation of the adaptive immune system neurological reflex modulates immune function of local versus systemic lymphatic tissue function through differential alteration of one or more neurotransmitters or neuropeptides in the lymphatic tissue (or lymphatic fluid) in response to the one or more energy pulses.

In exemplary embodiments, a method of neuromodulation of the adaptive immune reflex is provided that includes applying one or more energy pulses to a neuron of a subject to deliver sufficient energy to the neuron to neurally modulate a lymphatic tissue in response to applying the one or more energy pulses.

In exemplary embodiments, a method of neuromodulation of the adaptive immune reflex is provided that includes applying one or more energy pulses to a neuron of a subject via an electrode positioned to deliver sufficient energy to the neuron to modulate adaptive or innate immune function of contralateral lymphatic tissues such that a concentration or level of one or more neurotransmitters or neuropeptides in contralateral lymphatic tissues or contralateral lymphatic fluid is differentially changed in response to the one or more energy pulses.

In another embodiment, a method of neuromodulation of the adaptive immune reflex is provided that includes applying one or more energy pulses to a neuron of a subject via an electrode positioned to deliver sufficient energy to the neuron to modulate immune function of a lymphatic tissue such that a concentration of norepinephrine or epinephrine in the lymphatic tissue or a lymphatic fluid is increased at least 100% relative to a pre-stimulation baseline in response to the one or more energy pulses, wherein the one or more energy pulses are applied with an energy in a range of 0.5V to 10V.

In another embodiment, a method of neuromodulation of the adaptive immune reflex is provided that includes applying one or more energy pulses to a neuron of a subject via an electrode positioned to deliver sufficient energy to the neuron to modulate immune function of a lymphatic tissue such that a concentration or level of substance P in the lymphatic tissue or a lymphatic fluid is increased at least 50% relative to a pre-stimulation baseline in response to the one or more energy pulses, wherein the one or more energy pulses are applied with an energy in a range of 0.5V to 10V.

In another embodiment, a method of neuromodulation of the adaptive immune reflex is provided that includes applying one or more energy pulses to a neuron of a subject via an electrode positioned to deliver sufficient energy to the neuron to modulate immune function of a lymphatic tissue such that a concentration or level of vasoactive intestinal peptide in the lymphatic tissue or a lymphatic fluid is increased at least 50% relative to a pre-stimulation baseline in response to the one or more energy pulses, wherein the one or more energy pulses are applied with an energy in a range of 0.5V to 10V.

In another embodiment, a method of neuromodulation of the adaptive immune reflex is provided that includes applying one or more energy pulses to a neuron of a subject via an electrode positioned to deliver sufficient energy to the neuron to modulate immune function of a lymphatic tissue such that a concentration or level of neuropeptide Y in the lymphatic tissue or a lymphatic fluid is increased at least 100% relative to a pre-stimulation baseline in response to the one or more energy pulses, wherein the one or more energy pulses are applied with an energy in a range of 0.5V to 10V.

In another embodiment, a method of neuromodulation is provided that includes positioning an electrode on or near a lymphatic tissue of a subject at a location at which the electrode is capable of stimulating a neuron innervating the lymphatic tissue; applying one or more energy pulses to the tissue via the electrode to stimulate the neuron to modulate a lymphatic or immune function of the lymphatic tissue; assessing a state of the lymphatic or immune function within the subject after applying the plurality of energy pulses based on a characteristic associated with the lymphatic function or the immune function; and modifying a parameter of at least one of the plurality of energy pulses based on the state.

In another embodiment, a method for closed-loop neuromodulation is provided. The method includes applying one or more energy pulses to the tissue to stimulate the neuron to modulate a lymphatic or immune function of the lymphatic tissue; and assessing a state of the lymphatic or immune function within the subject after applying the plurality of energy pulses.

In another embodiment, a method for closed-loop neuromodulation is provided. The method includes controlling a pulse generator to apply one or more energy pulses to a neuron innervating a lymphatic tissue via an electrode and according to one or more parameters of at least one of the plurality of energy pulses to modulate a lymphatic function of the lymphatic tissue receiving information related to a condition or function of the lymphatic tissue; and changing the one or more parameters based on the information.

In another embodiment, a method for neuromodulation is provided that includes receiving one or more user inputs selecting a mode of operation for delivering energy pulses to an electrode to stimulate activity of lymphatic tissue; delivering the one or more energy pulses to the electrode from a pulse generator according to the mode of operation to cause the simulated activity of the lymphatic tissue; receiving one or more inputs related to the stimulated activity of the lymphatic tissue; and changing the mode of operation based on the inputs.

In another embodiment, a method for neuromodulation is provided. The method includes positioning an electrode at a location at which the electrode is capable of stimulating a neuron innervating the lymphatic tissue; applying one or more energy pulses to the tissue via the electrode to stimulate the neuron to modulate the lymphatic function of the lymphatic tissue; assessing a size of the lymphatic tissue after applying the plurality of energy pulses relative to a baseline size; and modifying a parameter of at least one of the plurality of energy pulses based on the size of the lymphatic tissue.

In another embodiment, a method of neuromodulation of the adaptive immune reflex is provided that includes applying one or more energy pulses to a neuron of a subject via an electrode positioned to deliver sufficient energy to the neuron to neurally modulate a lymphatic tissue to promote ingress or egress of cells from the lymphatic tissue or a lymphatic fluid in response to applying the one or more energy pulses.

In another embodiment, a method of neuromodulation is provided that includes applying one or more energy pulses to a neuron of a subject to modulate a nerve entering the lymphatic tissue, wherein the applying results in an increase in a subject's tissue or blood levels of one or more endogenous opiods relative to a pre-modulation control.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein:

FIG. 23A shows concentration of epinephrine in lymph tissue for a stimulated lymph node with an intact nerve, a stimulated lymph node with a severed nerve, and a control;

FIG. 23B shows concentration of norepinephrine in lymph tissue for a stimulated lymph node with an intact nerve, a stimulated lymph node with a severed nerve, and a control;

FIG. 23C shows concentration of dopamine in lymph tissue for a stimulated lymph node with an intact nerve, a stimulated lymph node with a severed nerve, and a control;

FIG. 23D shows concentration of neuropeptide Y in lymph tissue for a stimulated lymph node with an intact nerve, a stimulated lymph node with a severed nerve, and a control;

FIG. 23E shows concentration of substance P in lymph tissue for a stimulated lymph node with an intact nerve, a stimulated lymph node with a severed nerve, and a control;

FIG. 23F shows concentration of vasoactive intestinal peptide in lymph tissue for a stimulated lymph node with an intact nerve, a stimulated lymph node with a severed nerve, and a control;

FIG. 24A shows concentrations of epinephrine in a directly stimulated lymph node at different stimulation frequencies (with applied voltage held at 0.5 V);

FIG. 24B shows concentrations of norepinephrine in a directly stimulated lymph node at different stimulation frequencies (with applied voltage held at 0.5 V);

FIG. 24C shows concentrations of dopamine in a directly stimulated lymph node at different stimulation frequencies (with applied voltage held at 0.5 V);

FIG. 24D shows concentrations of epinephrine in lymph fluid taken after directly stimulating a lymph node at different stimulation frequencies (with applied voltage held at 0.5 V);

FIG. 24E shows concentrations of norepinephrine in lymph fluid taken after directly stimulating a lymph node at different stimulation frequencies (with applied voltage held at 0.5 V);

FIG. 24F shows concentrations of dopamine in lymph fluid taken after directly stimulating a lymph node at different stimulation frequencies (with applied voltage held at 0.5 V);

FIG. 25A shows concentrations of neuropeptide Y in a directly stimulated lymph node at different stimulation frequencies (with applied voltage held at 0.5 V);

FIG. 25B shows concentrations of substance P in a directly stimulated lymph node at different stimulation frequencies (with applied voltage held at 0.5 V);

FIG. 25C shows concentrations of vasoactive intestinal peptide in a directly stimulated lymph node at different stimulation frequencies (with applied voltage held at 0.5 V);

FIG. 25D shows concentrations of neuropeptide Y in lymph fluid taken after directly stimulating a lymph node at different stimulation frequencies (with applied voltage held at 0.5 V);

FIG. 25E shows concentrations of substance P in lymph fluid taken after directly stimulating a lymph node at different stimulation frequencies (with applied voltage held at 0.5 V);

FIG. 25F shows concentrations of vasoactive intestinal peptide in lymph fluid taken after directly stimulating a lymph node at different stimulation frequencies (with applied voltage held at 0.5 V);

DETAILED DESCRIPTION

Figure 1A:
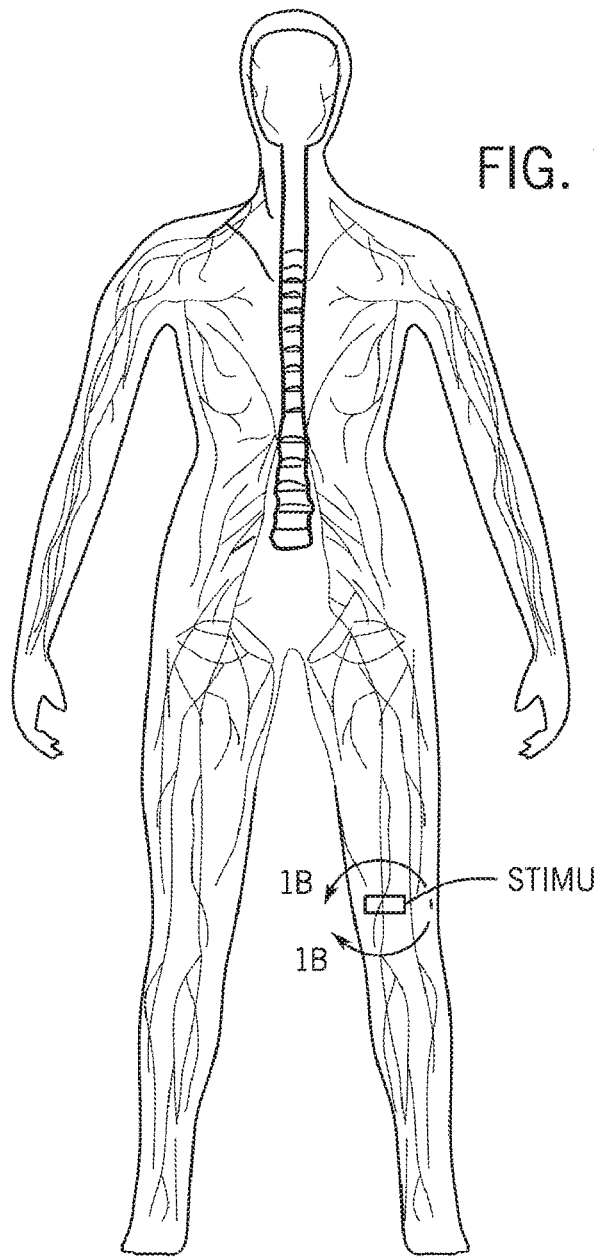
FIG. 1A is a schematic overlay of the central and peripheral nervous systems and the lymphatic system (picture shows secondary lymphatic structures and lymphatic vessels, but the system also includes primary lymphatic organs such as the spleen)

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Any examples or illustrations given herein are not to be regarded in any way as restrictions on, limits to, or express definitions of, any term or terms with which they are utilized. Instead, these examples or illustrations are to be regarded as being described with respect to various particular embodiments and as illustrative only. Those of ordinary skill in the art will appreciate that any term or terms with which these examples or illustrations are utilized will encompass other embodiments that may or may not be given therewith or elsewhere in the specification and all such embodiments are intended to be included within the scope of that term or terms. Language designating such non-limiting examples and illustrations includes, but is not limited to: "for example", "for instance", "such as", "e.g.", "including", and "in one (an) embodiment".

The present techniques relate to differential neuromodulation of an adaptive immune reflex to cause activation of cell or tissue-based physiological effects in lymph and surrounding tissue. For example, immune cells are known respond to chemical stimuli, such as the neurotransmitters/neuropeptides released by nerves (released in response to action potentials and bioelectrical activity). However, the extent to which these stimuli modulate immune function compared to prototypical cytokine and inflammatory signaling remains unknown. In addition, the locations and tissue microenvironments where these neuro-immune signals may be most impactful are not known. While the rough anatomy of neural innervation in lymphatic tissue has been known, the functional role that these nerves play in immune cell and tissue function has not been determined. Bulk pacing of the peripheral nerves innervating lymphatic vessels, and the electrical stimulation has been shown to alter lymph flow in a manner reminiscent of vasoconstriction/vasodilation in blood vessels. However, the functional outcome of neurotransmitter and neuropeptide release on immune cells within the lymphatic systems and lymph tissues/organs (including the cortical and paracortical regions involved with B and T cell related activity) has not been determined. Most importantly, the ability of the nervous system to orchestrate an adaptive immune response across a network of nerves innervating multiple lymph tissues/organs, or a researcher's ability to differentially modulate this effect has not been shown.

Vagus nerve stimulation has been used to excite the cholinergic anti-inflammatory pathway. In this pathway, the efferent arm of the vagus nerve innervates the celiac ganglion, where the splenic nerve projects to the spleen. This splenic projection releases acetylcholine within the spleen, which interacts with the nicotinic AChR on macrophages (and other cytokine producing cells). This interaction inhibits TNF (and other pro-inflammatory cytokine) production in spleen, producing a systemic anti-inflammatory response through modulation of the innate immune system.

However, the immune system is complex, and it is likely that neural reflexes modulate more than just systemic expression of molecules associated with innate immunity. Lymph nodes and lymphatic tissue represent a prime physiological target for investigation of neuroimmune modulation. The lymphatic tissue is a primary site of control over adaptive immunity, as antigen presenting cells (e.g. dendritic cells) home to the lymph upon antigen activation, and naïve lymphocytes home to lymph during inflammation. These two mechanism work to dramatically increase the opportunity for a naïve lymphocyte to interact with its cognate antigen. These cell migration or homing processes may be activated through changes in either the immune cell phenotype (i.e. up regulation of proteins associated with intra- and extravasation), the phenotype associated with lymphatic or vascular endothelium at the lymph node entrance (i.e. surface proteins associated with immune cell-endothelial interactions or endothelial layer permeability), or the phenotype associated with lymphatic endothelium at the lymph node exit. These cell homing processes may also be altered by modulating bulk flow of lymphatic fluid. Indeed, one of the remaining open questions in immune biology is exactly how a few memory cells mount a dramatic and rapid response to antigens that are present in only a local tissue environment (and may be meters away from the nearest memory cell).

In addition to immune cell migration, the microenvironment of the lymph compartment is associated with cell fate upon cognate antigen binding and activation. In general, a microenvironment rich in "inflammation-associated" proteins and signaling molecules drives an activated lymphocyte or immune cell into an "effector phenotype". Effector cells are typically expressing proteins associated with "fighting an infection or foreign invader". As an example, effector T-cells include cytotoxic T cells or T-helper cells capable of inducing maturation of B-cells or activation of macrophages. In general, a microenvironment rich in "anti-inflammatory" proteins and signaling molecules produces "suppressor phenotypes". Suppressor cells are typically expressing proteins associated with "inhibiting active immune responses". As an example, suppressive T-cells are regulatory T-cells which help to decrease excessive immune reaction to "self-antigens" (i.e. maintain immune tolerance). These examples represents only a few of the immune cell (and supporting cell) phenotypes that depend on the state of the dynamic lymph microenvironment.

Lymph nodes (and lymph-associated tissues) are innervated by neurons; early studies revealed a breadth of neuronal sub-types within the lymph compartment, including neurons staining positive for a variety of neurotransmitter and neuropeptide receptors. In addition, the lymph node is structured with distinct immune functions being compartmentalized into specific tissue architectures. Barrier tissues, such as high endothelial venules function to modulate immune cell entrance/exit rates from the lymph tissue. Paracortical and cortical areas hold T-cells, while central follicles house B-cells. Supporting cells include fibrillary structures that allow cell migration between "zones", and resident antigen presenting cells which may further modulate lymphocyte function and trafficking. Naïve lymphocytes and cells traverse these regions regularly during their circulation from tissue through the lymphatic and circulatory systems. Activated cells respond to migratory signals (originated from surrounding cells) and move from one lymph compartment to the next to complete their function. As an example, B-cells that become activated and proliferate within the follicular regions migrate to marginal zones (between T and B-cell rich areas of the lymph). In the marginal zone, the B-cell may interact with a T-helper cell that provides signals necessary for full maturation into a plasma cell (i.e. antibody producing cell); the matured plasma cell then migrates to efferent lymphatic and medullary sinus structures and begins producing antibodies that are secreted into circulation. Although neural innervation of these structures are known; there is little understanding of the functional significance of neural signaling in these local lymph microenvironments. While neurotransmitter and neuropeptide receptors are shown to exist at very specific locations within the lymph node architecture/compartments, it is not evident that those receptors would function to relay information back to the central nervous system (i.e. receptors may merely serve for local release of neurotransmitter/ neuropeptide under certain conditions, which act (like cytokines) as local immunomodulators). Still, the existence of functional neural reflex circuits (i.e. fast/local reflexes between lymph compartment and/or slow/global circuits between lymph compartments and the central nervous system) would have a profound impact on the study and therapeutic application of neuroimmune interactions.

To date, a few studies have demonstrated that in vivo injection of molecules typically classified as neurotransmitters or neuropeptides may modulate local immune activity. For instance, norepinephrine is thought to alter lymphocyte migration out of the lymphatic system, and VIP is thought to induce regulatory function/phenotype in T-cells. However, these functional outcomes are yet to be shown via direct neural stimulation (in which release profiles and concentrations are controlled by nerve location and synaptic activity), instead immune modulation is shown via systemic injections of high concentrations of the neural signaling molecules. Therefore, the importance of neural activity in local modulation of these immune processes remains unknown. More importantly, because investigation has relied on altering concentrations of neural signaling molecules at a large or systemic scale, it is unknown whether local neural reflexes may provide a concerted or coordinated response to immunomodulation (through long-range neural signaling between lymph tissues). Therefore, it remains possible that a web of afferent and efferent neurons provides a mechanism for long-range concerted response to local immune insults across lymphatic structures. These neural reflexes may modulate immune activity across several length scales, and be leveraged therapeutically through specific differential stimulation.

The spinal motor system represents a good analogy for hypothesizing and testing the various neural reflexes that may exist within the immune or lymphatic tissues. The neural reflex circuits within the spinal motor system allow the CNS to effectively measure force and length of a muscle (and therefore provide a correct motor response for a desired perturbation). Sensory or afferent neurons within the muscle spindle are able to excite alpha motor neuron activity. Golgi tendon afferents are able to inhibit (via interneurons within the spinal column) alpha motor neuron activity. In addition, gamma motor neurons are able to control the length of the muscle spindle itself, and therefore set the sensitivity of the spindle afferents. These neural reflexes are responsible for controlling the canonical hammer tap reflex of the knee tendon, in which tapping the knee tendon causes stretching of the muscle sensory afferents and concerted excitation/ relaxation of the extensor and flexor muscles of the leg respectively (with the inhibitory spinal interneuron responsible for the opposite flexor/extensor response to perturbation). It can be postulated that since nerve synapses exist within lymphatic tissue and neural signaling molecules seem to alter immune activity, there may be a similar (but yet unknown) reflex associated with neuro-immunomodulation of immune and lymphatic tissue. Furthermore, understanding this circuit may allow differential modulation of adaptive immune responses across lymph/immune tissue networks.

Sticking with the motor neuron analogy, it is also known that cortical neurons can directly alter motor neurons responding to the canonical muscle reflexes. In this case, actively thinking about opposing a muscle stretch or perturbation (before the stretch occurs) changes the latency of the muscle response to the stretch. This has been attributed to the existence of a second motor reflex pathway. The spinal column reflex discussed above is named "the short-latency response pathway", while this other reflex that is dependent on cortical neural activity is named "the long-latency response pathway". The afferent inputs (from the muscle spindle) associated with the long-latency pathway must pass through additional interneurons in the dorsal column nuclei and thalamus, and thus provides a reflex with a delayed response (or latency) compared to the spinal reflex The result of these two pathways is the existence of both a short-latency "involuntary response" and a long-term "voluntary response" associated with a muscle stretch perturbation. Again, it can be postulated that since nerve synapses exist with lymphatic tissue and neural signaling molecules seem to alter immune activity, there may be a similar (but yet unknown) cortical reflex or neural pathway that provides control over neuro-immunomodulation in immune and lymphatic tissues. Furthermore, understanding this circuit may allow differential modulation of adaptive immune responses across lymph/immune tissue networks, and additional information on cortical control (such as the possibility of "immune memory" or information stored in the cortex about specific inflammatory or antigen perturbation events).

None of the current findings demonstrate the ability of the nervous system to conduct a concerted adaptive immune response to local immune perturbations/or insults. Systemic neuroimmune reflexes, such as the cholinergic anti-inflammatory pathway, have been discovered and applied. However, these pathways involve global/systemic control of innate immune response, and would not be a mechanism for mounting a concerted adaptive immune response across the vast system of immune and lymphatic tissue within the body. Uncovering and applying such a local adaptive immune reflex would have profound implications in both basic science and translational medicine.

As discussed, the lymph node is a compact immune tissue that is separated into distinct compartments each containing distinct immune cell sub-types with different immune functions. Further, these compartments are innervated by different types of neurons. However, the neural signals (action potential frequency, stimulation intensity) required to elicit a functional change in immune cell state is unknown. Certain innervated lymph node compartments include areas dominated by T cells, in which dendritic cells migrate and present antigen to the cells for activation. Innervation also follows blood vessels, some of which are responsible for controlling the migration/entrance of immune cells from peripheral tissues. For example, lymphocytes in the blood stream can enter into a lymph node through high endothelial venules (HEVs). Furthermore, the rates at which lymphocytes and fluids enter and exit a lymph node influence the lymph node's volume. Within the lymph node, support cells and tissue play a role in regulation of immune cells responding to self-antigen; and maintenance of immune cell tolerance. Other microenvironments within the lymph node effect the phenotype of immune cells once activated by a specific cognate antigen, for instance endothelial cells within the exit vessels of the lymph node provide an anchor location and microenvironment for activated plasma cells which release antibody to the bloodstream. As an additional effect, lymph nodes and the lymphatic system function to transport, filter, and drain lymph fluid that arises from the interstitial fluid of upstream tissues. For example it is known that the protein composition of efferent lymph fluid for a lymph node is typically higher than its afferent lymph fluid. The rate of flow of afferent and efferent lymph for a lymph node is modulated and involves contractions of smooth muscle cells of lymphatic vessels (0.6 to 10 beats per minute), lymphangion structures and even by the contraction of lymphatic smooth muscle surrounding the exterior wall of the lymph node (0.5 to 1 beat per minute). Neuromodulation of lymph tissue may alter the drainage rate and/or the population of cells in the drained fluid. These (and other) adaptive immune processes that occur within lymph tissue are related to a large number of diseases, including infections, inflammatory/auto-immune diseases, allergies, and the immune response to tumors or foreign bodies (transplants and implants). In one embodiment of the disclosed techniques, local stimulation of specific nerves upstream of, adjacent to, or within the lymphatic tissue results in 1) downstream immune modulation within the target lymph tissue and 2) orchestrated or coincident immune modulation in neighboring lymph tissue through an adaptive immune reflex pathway. Provided herein are techniques for differential immunomodulation across lymphatic networks based on stimulation of the adaptive immune reflex.

As provided herein, neural modulation or neurally modulating a subject refers to the application of energy to a neuron or a nerve via an introduced energy source, which may be an internal or implanted energy source or an energy source external to the subject. The energy source may be a pulse generator that generates electrical or other energy pulses that are applied to the nerve via one or more electrodes. Neural modulation (i.e., neurally modulating) may include the neurostimulation, or application of energy that activates or increases the nerve or nerve function. Neuromodulation may also include the application of energy that blocks or decreases the nerve or nerve function. It should be understood that neural modulation may be achieved by additional or alternative techniques. However, in the context of the present disclosure, the neural modulation is achieved at least via the application of energy via one or more electrodes positioned such that the application of energy pulses modulates a neuron or nerve at a desired location. In particular embodiments, the electrode may be positioned within a lymphatic tissue, proximate to (e.g., on or near) a nerve innervating lymphatic tissue, or on an exterior surface of the subject's skin (or mucosal tissue) at a location such that applied energy activates the neuron or nerve transdermally.

To that end, the disclosed neuromodulation techniques may be used to locally or differentially modulate the adaptive immune reflex. FIG. 1A is a schematic representation or overlay of the central nervous system, the peripheral nervous system, and the lymphatic system. An adaptive immune response in a neural pathway facilitates concerted or orchestrated modulation of an adaptive immune response across the vast lymphatic system via neural signaling. Neuromodulation of the adaptive immune response may be performed on any nerve innervating a specific lymphatic tissue (or lymph node, shown in FIG. 1B), in which the adaptive immune response may be modulated to achieve a different immune response or outcome than that of the surrounding tissues. The stimulation may include stimulation of sensory/afferent and/or efferent/effector nerve fibers. The modulation site may be any suitable nerve location that modulates an immune and/or lymphatic response as provided.

Figure 1B:
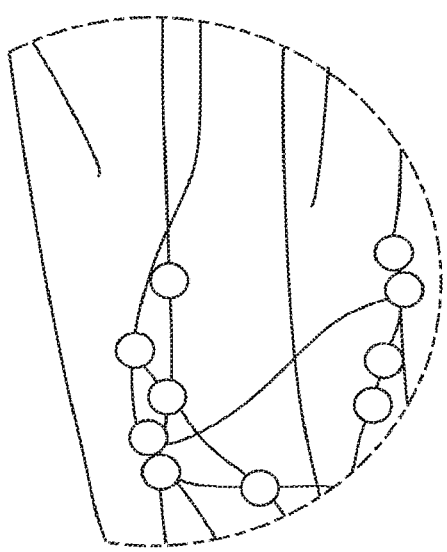
FIG. 1B shows a potential site for electrical stimulation or neuromodulation located on a peripheral nerve between the lymphatic system and the CNS.
Figure 1C:
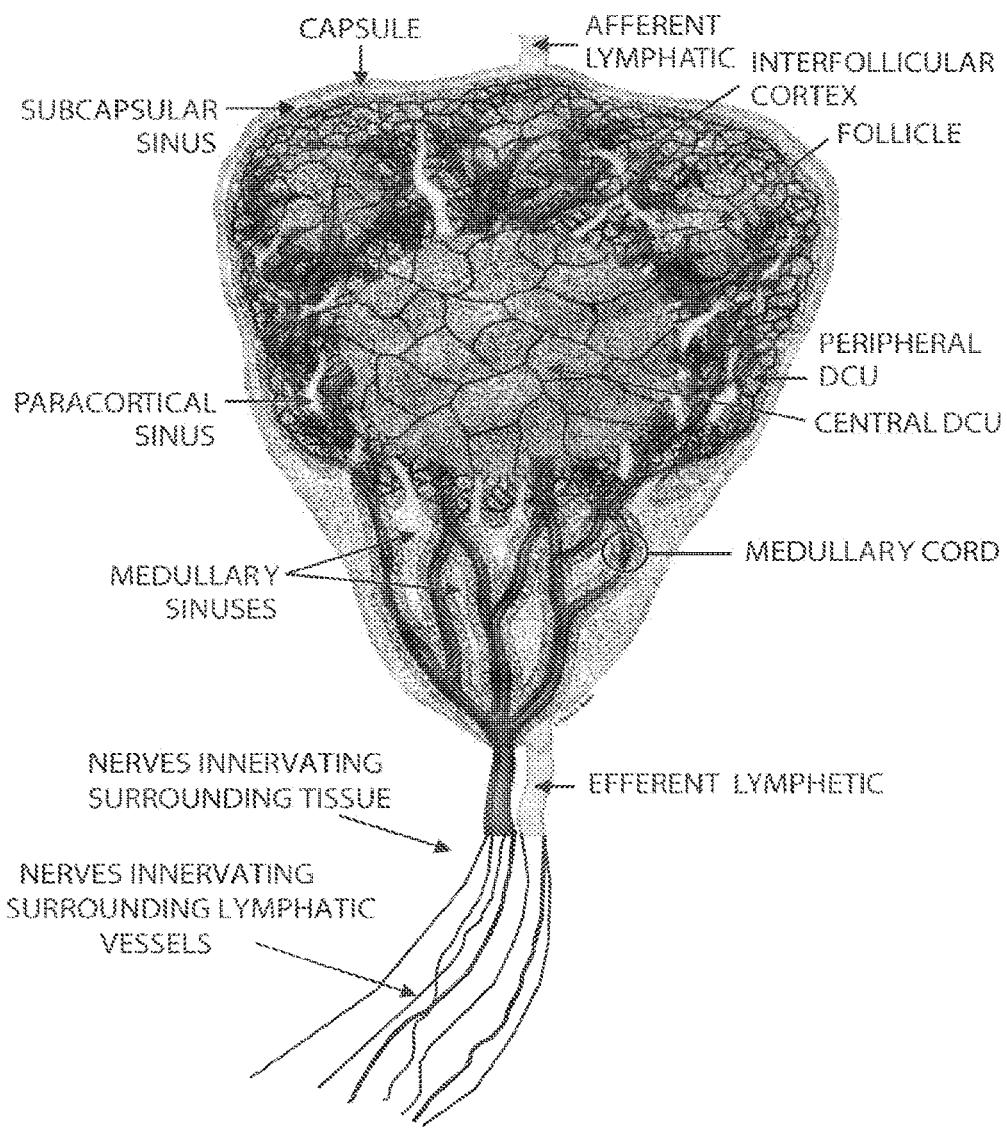
FIG. 1C is a schematic of potential neural innervation of a secondary lymph tissue (i.e. lymph node)

FIG. 1B is a schematic of what is known about neural innervation of the lymph node environment. Different nerve types (including sympathetic or catecholamine neurons and neuropeptide neurons) have been observed at different location within the lymph node architecture. These nerves innervate the lymph node, shown in FIG. 1C at the apex (following blood vessels) and terminate in different areas of the lymph node, including the paracortex, interfolicular areas, and medullary sinuses. These nerves travel along the lymphatic vessels and innervated the blood and lymphatic vessels that connect the lymph nodes within the lymphatic system as well.

Figure 2A:
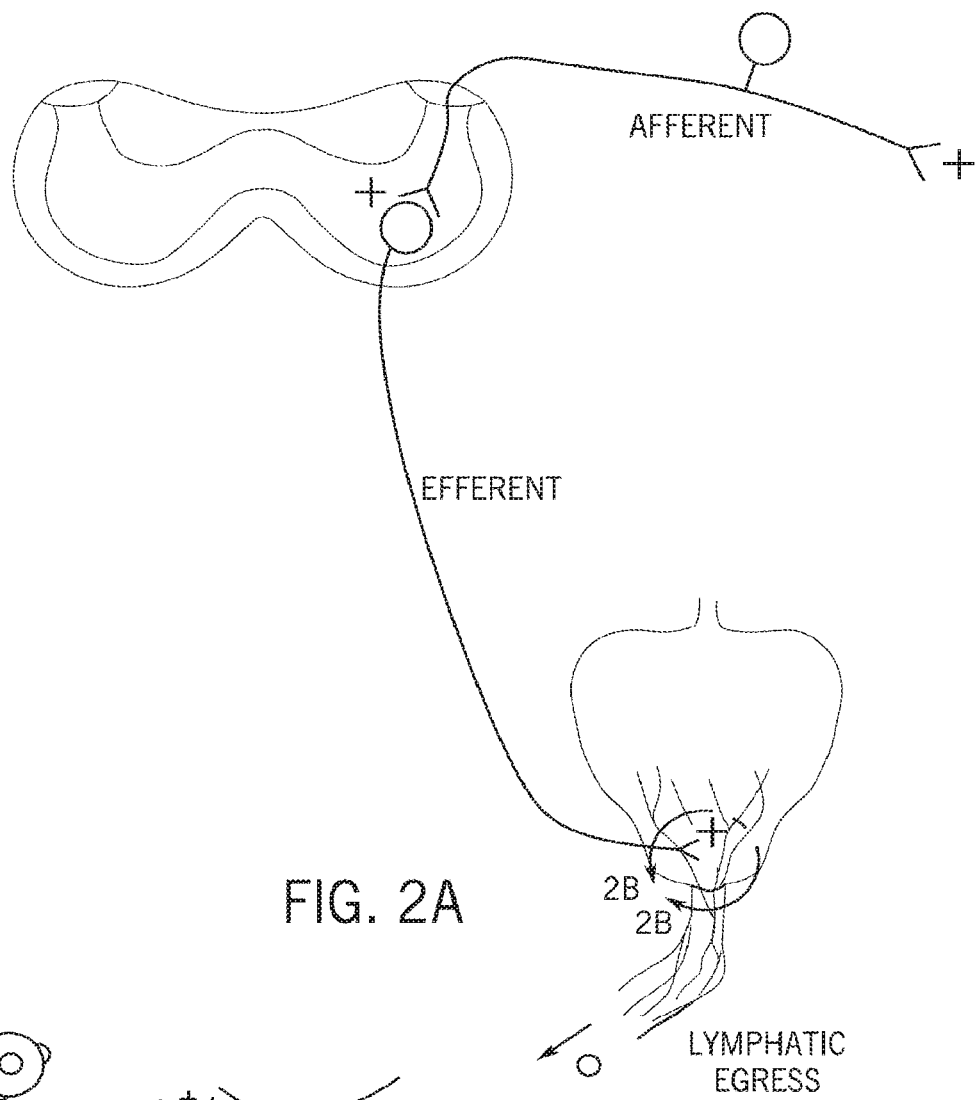
FIG. 2A is a schematic of one of the simplest types of adaptive immune reflexes that may exist within the lymphatic system, including an afferent neuron that controls the neural output of an efferent neuron which innervates a specific local lymph node compartment for modulating an adaptive immune process.
Figure 2B:
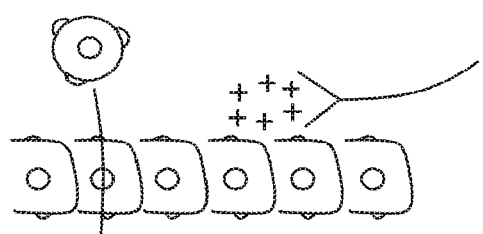
FIG. 2B shows one example adaptive immune process with the egress of lymphocytes from the lymph system, which would control the timing of lymphocyte screening within the node)

In certain embodiments, neuromodulation modulates an adaptive immune reflex. An adaptive immune reflex may involve stopping lymphocyte egress from a lymph node due to afferent neuron activity caused by inflammation or the presence of antigen. An increase in lymphocytes in the lymph node may increase antigen screening. FIG. 2A shows a schematic of one potential pathway for an adaptive immune reflex. In this simple pathway example, an afferent neuron in lymphatic or surrounding tissue, e.g., a sensory neuron, communicates to an efferent neuron that innervates a specific location within the lymph node architecture. As an example, this may be the endothelium within the medullary and inter follicular areas that are responsible for gating lymphocyte egress from the lymph node. Signaling from the afferent neuron (modulated by inflammatory molecules or antigens) may affect the firing of this efferent neuron, and alter local concentrations of neurotransmitters or neuropeptides (that may modulate the rate of egress or lymphocytes through the endothelial barrier, e.g., by altering permeability or by affecting exit sinusoids). FIG. 2B is a schematic drawing of the pathway altering endothelial barrier permeability to a lymphocyte to permit crossing of the barrier Such an adaptive immune reflex may be important to allow rapid decrease in lymphocyte egress upon infection, which may quickly increase lymphocyte screening of antigen from antigen presenting cells migrating to the lymphatic compartment.

Figure 3:
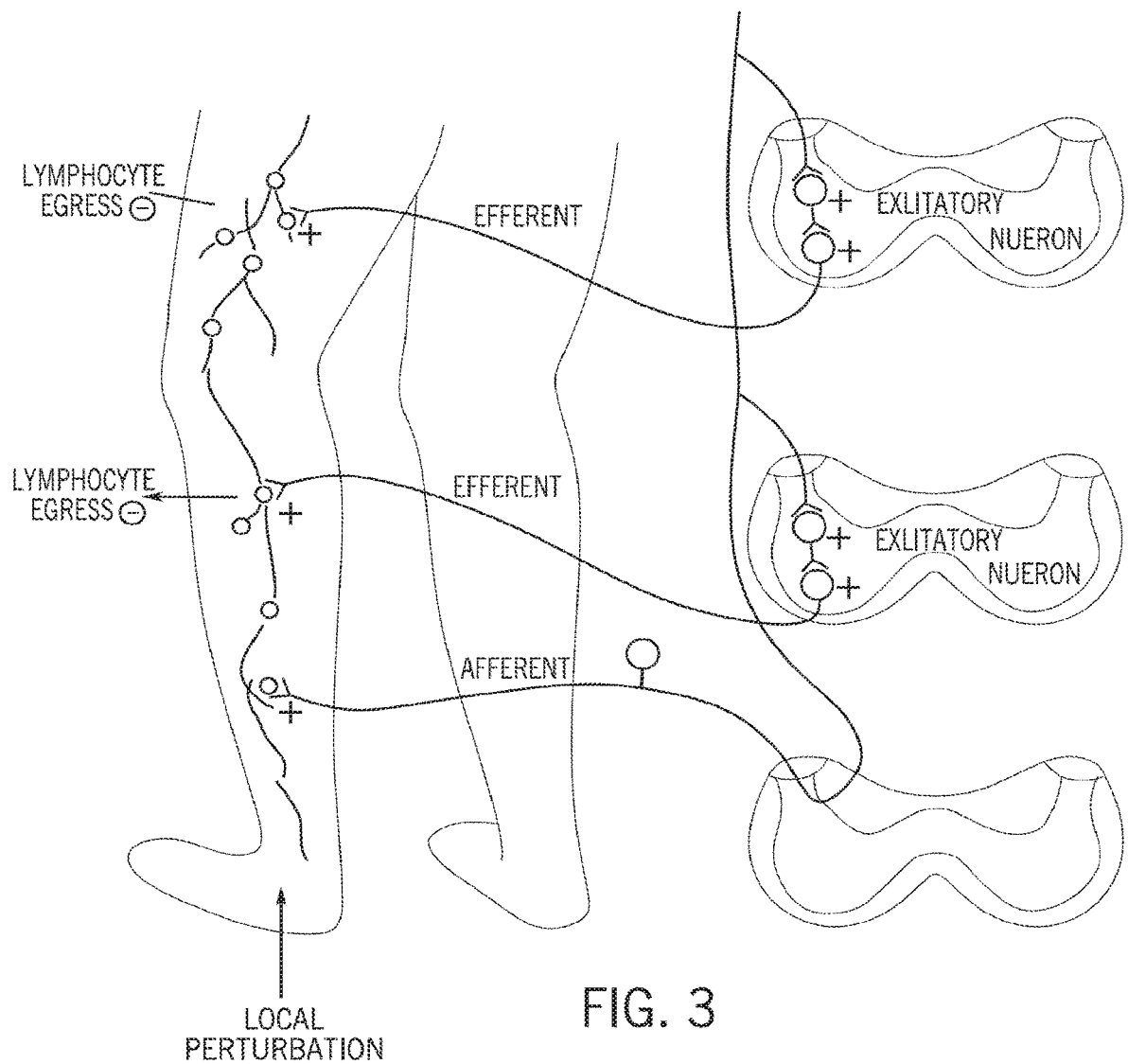
FIG. 3 shows an additional level of adaptive immune control that may exist within an adaptive immune reflex via centrally projecting afferent neurons that may traverse multiple levels of the spinal column or lymphatic system, and enable coordinated modulation of lymphocyte egress across multiple lymph nodes.

FIG. 3 represents another example neural pathway for an adaptive immune reflex, in which the afferent neuron (signaling inflammation or antigen presence) continues into and up the central nervous system. In this case, neural signaling from that nerve may act to provide a coordinated or orchestrate adaptive immune response by signaling to multiple efferent neurons, innervating multiple lymph nodes or lymphatic tissue across the network. As an example, lymphocyte egress from lymph nodes across an entire section of the lymphatic system may be decreased due to the presence of a single local perturbation or stimulation, e.g., local inflammatory or infection event. Afferent neural input to the adaptive immune reflex may travel up the spinal column to coordinate the immune reflex across an entire lymphatic region, e.g., stimulation of the foot may alter lymphocyte egress in the entire leg.

Figure 4:
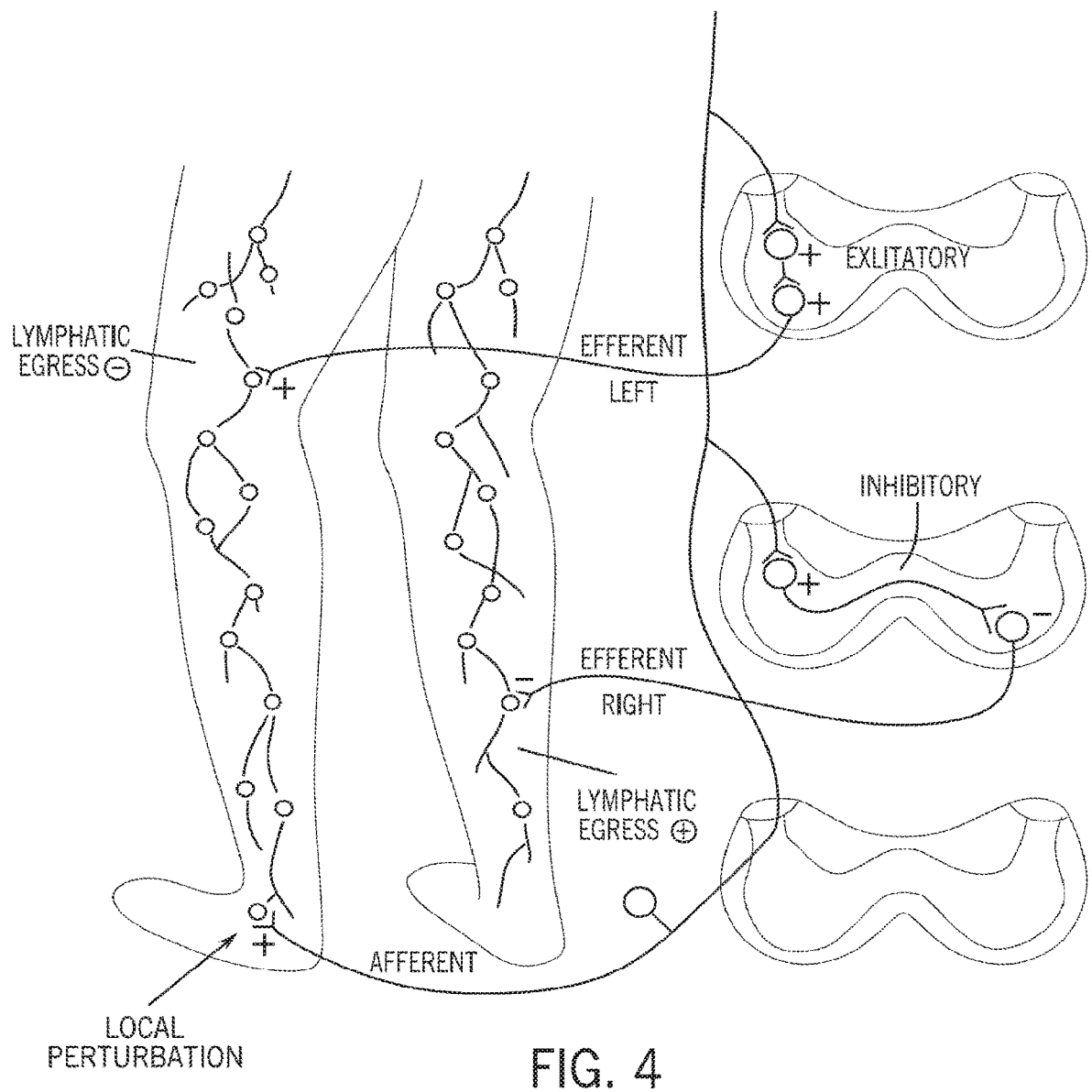
FIG. 4 shows an additional level of adaptive immune control that may exist within an adaptive immune reflex via centrally projecting afferent neurons that may traverse multiple levels of the spinal column of lymphatic system to permit differential modulation of contralateral lymph structures, e.g. decrease of lymphocyte egress at the site of inflammation/antigen perturbation, but lymphocyte mobilization from lymph nodes in other remote lymphatic regions.

FIG. 4 represents another example neural pathway for an adaptive immune reflex, in which the afferent neuron (signaling inflammation or antigen presence) continues into and up the central nervous system. In this case, neural signaling from that nerve may act to provide opposite adaptive immune outcomes at different location within the lymphatic system. As an example, lymphocyte egress within the lymphatic system surrounding a local inflammatory or antigen insult may be decreased (to allow for rapid or increased lymphocyte screening within those lymph nodes), but lymphocyte egress in distance portions of the lymphatic system may be increased in order to mobilize lymphocytes toward the infected area. As shown, this type of action may be produced through interneurons which excite effector neurons in one part of the lymphatic system, but inhibit efferent neurons innervating other/distant areas.

Figure 5:
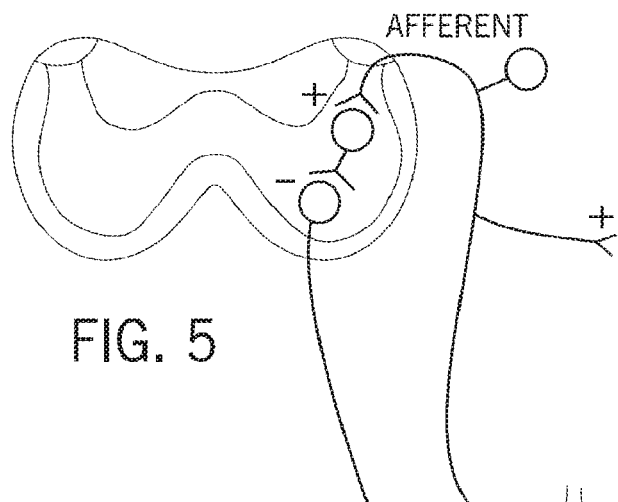
FIG. 5 shows an additional level of adaptive immune control that may exist within an adaptive immune reflex via inhibitory neurons that may exert autogenic inhibition of the efferent neuron, allowing timed secession of the neural signal caused by the initial inflammatory/antigen perturbation and in which the inhibitory signal may be due to afferent signaling from the same nerve causing the initial response within or outside the lymph node environment.

FIG. 5 represents another example neural pathway for an adaptive immune reflex, in which the afferent neuron (signaling inflammation or antigen presence) excites an inhibitory neuron, which decreases activity of the efferent nerve in the adaptive immune reflex. This autogenic inhibition may be utilized in conjunction with the simple neural pathway described in FIG. 2A to provide feedback or opposing neural signals to offset an initial immune outcome (as shown using lymphocyte egress as an example). As shown afferent signaling may originate from tissue activity in either lymph or surrounding tissues (thus, conveying information about the adaptive immune response at various stages). After a long inflammatory response or local changes in lymph node environment (i.e., cognate antigen recognition and lymphocyte proliferation), a different afferent/sensory neuron may form a dissynaptic reflex, where an inhibitory neuron acts to shut down the initial responses and again allow lymphocyte egress from the lymph node. This would allow a feedback control mechanism for the initial response.

Figure 6:
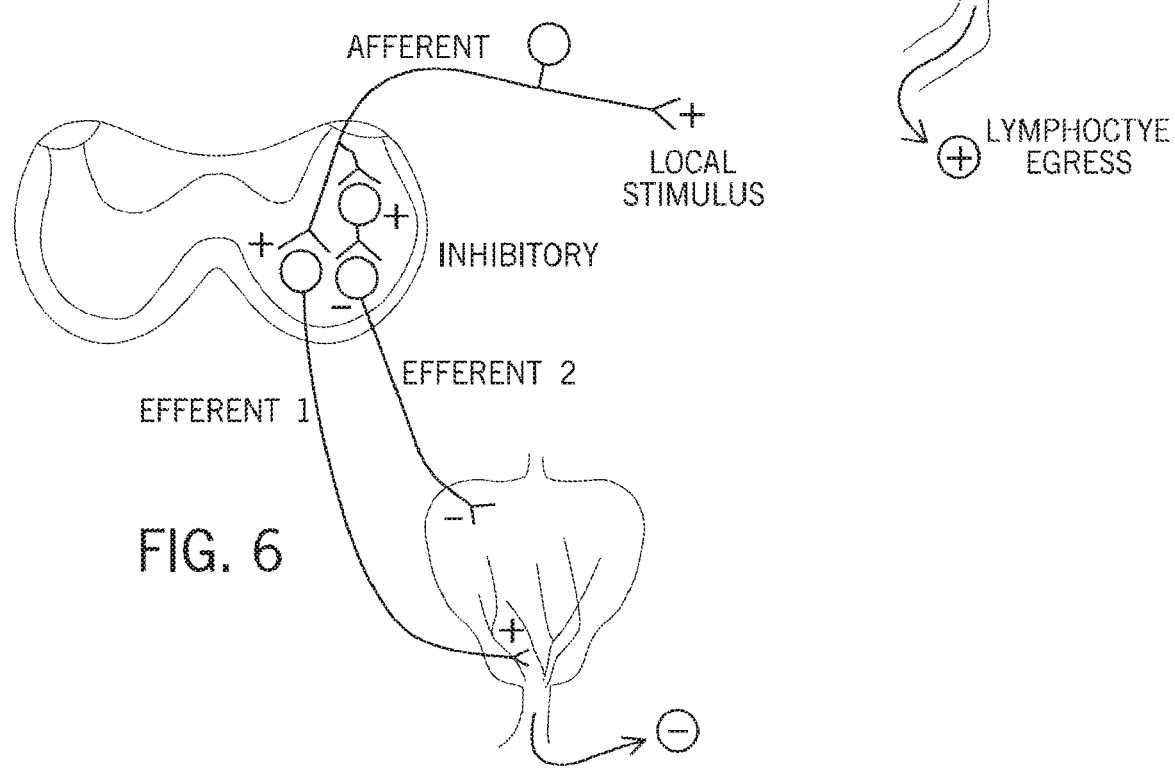
FIG. 6 shows an additional level of adaptive immune control that may exist within an adaptive immune reflex in which one neuron may exert reciprocal inhibition of the efferent neuron by synapsing with both the efferent neuron and a second efferent neuron through an inhibitory interneuron to allow for differential modulation of immune activities within different lymph compartments, e.g., to act to decrease neural output to a different part of the lymph node.

FIG. 6 represents another example neural pathway for an adaptive immune reflex, in which the afferent neuron (signaling inflammation or antigen presence) excites neural pathways associated with two different efferent neurons. An inhibitory neuron may be present in between the afferent nerve and one of the efferent pathway, allowing a reciprocal inhibition of the adaptive immune response and/or differential neuromodulation in different location within the lymph tissue/node. A reciprocal inhibition reflex through a unilateral inhibitory neuron may act to decrease neural output to a different part of the lymph node. For instance, in FIG. 6, efferent 1 may act to decrease lymphocyte egress, while efferent 2 may decrease neurotransmitter levels in the follicle or germinal center, thus, promoting a more effector immune cell phenotype, upon cognate antigen recognition.

Figure 7:
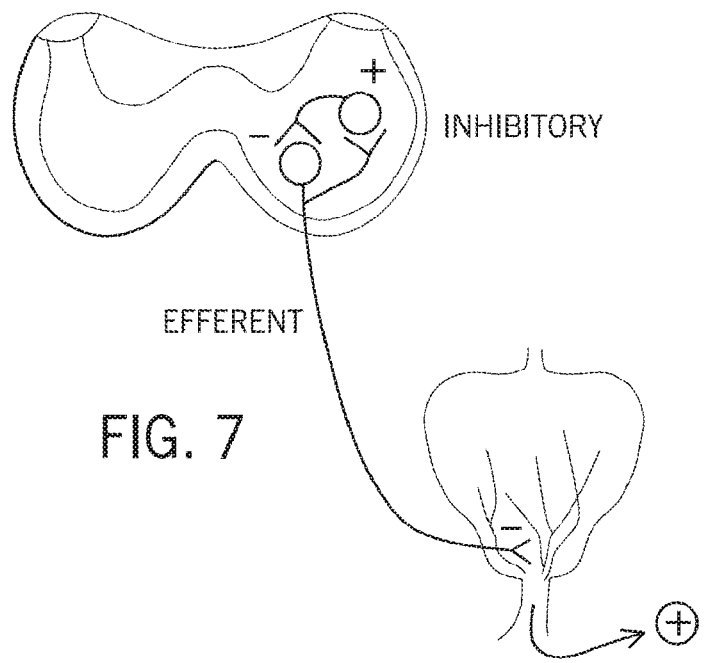
FIG. 7 shows an additional level of adaptive immune control that may exist within an adaptive immune reflex in which signaling from the efferent neuron may feedback onto an auto-inhibition loop through an inhibitory interneuron to allow self-regulation of the timing and/or magnitude of the adaptive immune perturbation.

FIG. 7 represents another example neural pathway for an adaptive immune reflex, in which efferent nerve signaling feeds back onto an inhibitory neuron and enables self-inhibition during neural firing. This configuration of a reflex pathway would allow self-regulation, where efferent nerve firing would feedback on itself to limit the duration and/or magnitude of the neural signal in the lymph tissue/node. Special inhibitory cells in the spinal column may inhibit the very same efferent neuron that is firing, thus providing a self-regulation. For example, an initial decrease in lymphocyte egress shuts down after some time due to negative feedback from the inhibitory neuron.

Figure 8:
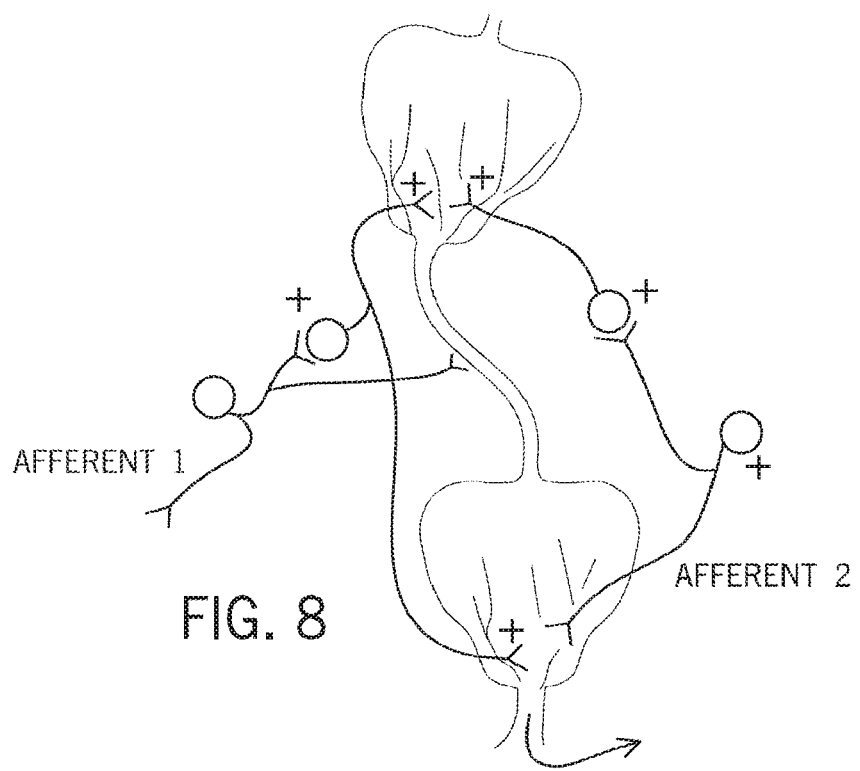
FIG. 8 shows how the different mechanisms for adaptive immune reflex may exert control across a local lymph network, without direct interaction with the CNS or spinal column.

FIG. 8 represents another example of neural pathways for an adaptive immune reflex, in which the neural pathway is entirely contained within the peripheral nervous system (and does not include neurons within the spinal column or CNS). These neurons may be associated with excitatory and/or inhibitory neurons associated with just lymph or surrounding tissue, and may be connected by nerves traveling with lymphatic vessels. This network of nerves may contribute to reflexes discussed above (i.e. reciprocal, autogenic, crossed, coordinating, and recurrent reflex circuits) and communicate solely within the neural network surrounding the peripheral lymphatic tissue. A network of afferent/efferent neurons may synapse directly within the lymphatic tissue and vessels, and enable neuronal signaling between neighboring lymph nodes along lymph specific pathways.

Figure 9:
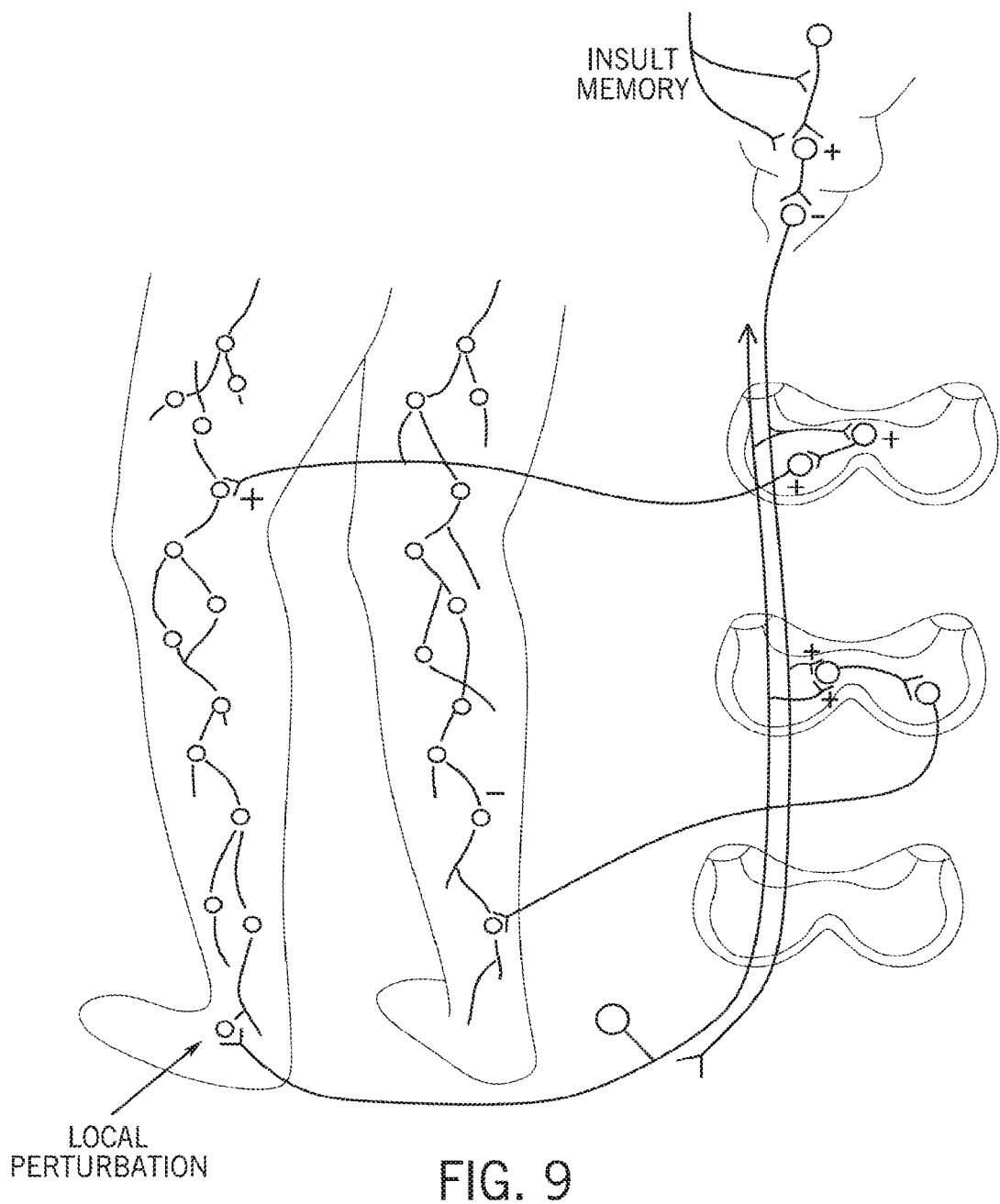
FIG. 9 shows an additional level of adaptive immune control that may exist within an adaptive immune reflex. In this case, signaling from the local reflexes may be directly connected to pathways that extend through the brain stem and higher level brain regions.

FIG. 9 represents another example of a neural pathway for an adaptive immune reflex, in which the neural pathway projects throughout the CNS (including neurons with higher level brainstem or cortical pathways). This type of long-loop reflex may enable inhibition of portions of local adaptive immune reflexes through central nerve signaling. For instance, as depicted a signal of systemic inflammation to a brainstem or higher level ganglia neuron may signal to inhibit the crossed mobilization reflex described in FIG. 4. This would allow for mobilization of lymphocytes from far off lymph tissue to move toward local infections during standard conditions, but elimination of this mobilization when the body is fighting a system infection or insult. Additional effects of higher level CNS input into an adaptive immune reflex would be to provide "immune memory" or cortical participation in the coordination and orchestration of response to specific inflammatory or antigenic stimuli. As shown, insult memory may be mediated by signals that represent systemic inflammation that are the result of the long-loop adaptive immune reflex. Higher level reflexes may allow inhibition of parts of the response. Longer cortical or CNS loops may promote coordination of local immune reflexes of systemic physiological conditions. For example, a cortical or CNS loop signaling chronic or systemic inflammation may inhibit a crossed mobilization reflex. As provided herein, neuromodulation may result in such local inhibition to treat systemic inflammation or may be used to mobilize previously inhibited local responses.

Figure 10:
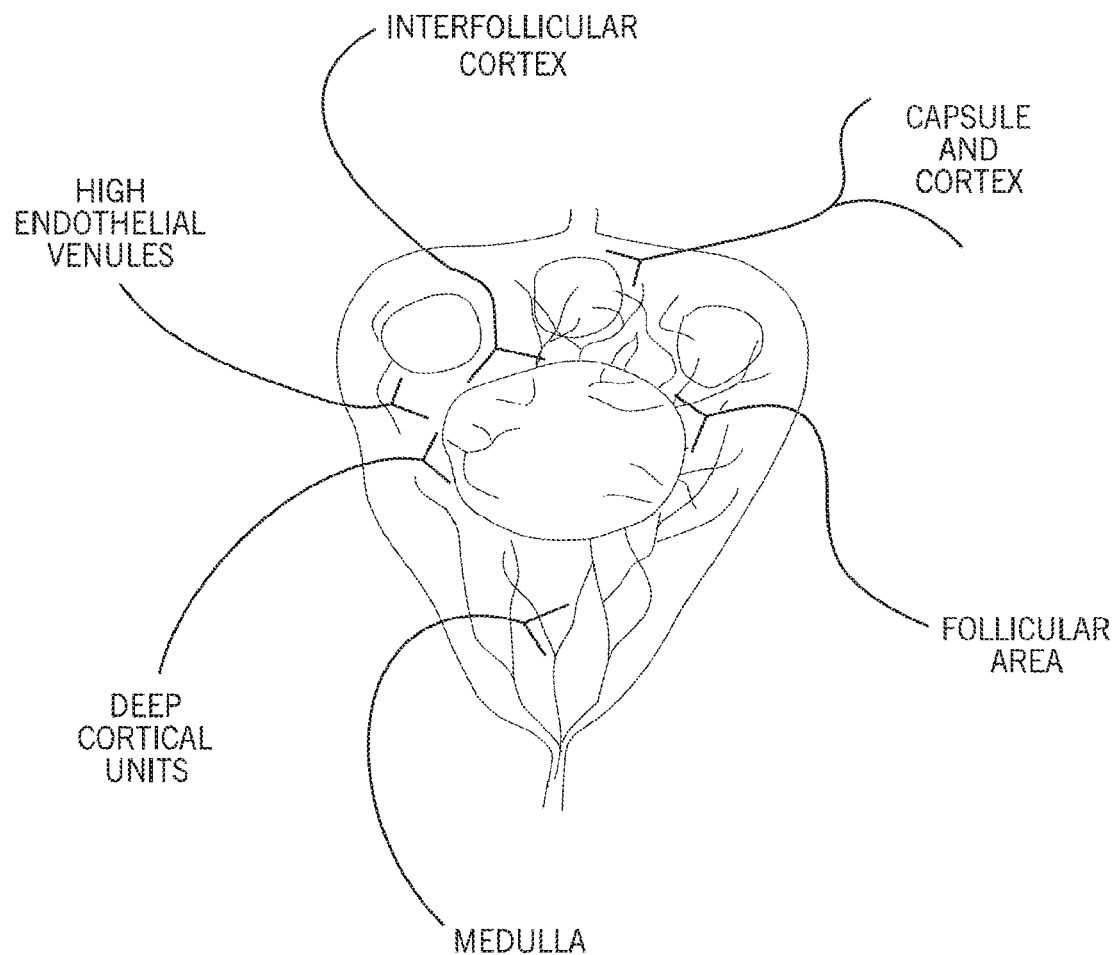
FIG. 10 shows example of the many areas within lymph tissue that may be effected by the adaptive immune reflex, and specific adaptive immune processes that may be modulated through neural modulation at each area.

FIG. 10 depicts how nerve endings within different locations within the lymph tissue/node architecture may have dramatically different effects on the adaptive immune system. Innervation at the high endothelial vessels may enable neuromodulation of the influx of lymphocytes from the blood and into the lymph compartment, e.g., neuromodulation may promote egress or ingress depending on the stimulating or blocking frequencies used. Nerves within the capsule and cortex may enable neuromodulation of processes governing the ingress of antigen presenting cells or permeability of the reticular cells network that filters lymph fluid. Innervation of the follicular area may enable modulation of B-cell homing, B-cell interaction with antigen presenting cells, or B-cell phenotypes upon activation. Nerves within the deep cortical units my allow modulation of T-cell homing, T-cell interaction with antigen presenting cells, or T-cell phenotype upon activation. Innervation of the interfollicular areas may allow modulation of T-cell/B-cell interactions, including T-cell involvement in the maturation of activated B-cells into antibody producing plasma cells. Nerves within the medullary areas may enable neuromodulation of lymphocyte and/or antigen presenting cell egress from the lymph node, and/or modulate phenotype of cells within the area (such as anchored plasma cells).

Figure 11:
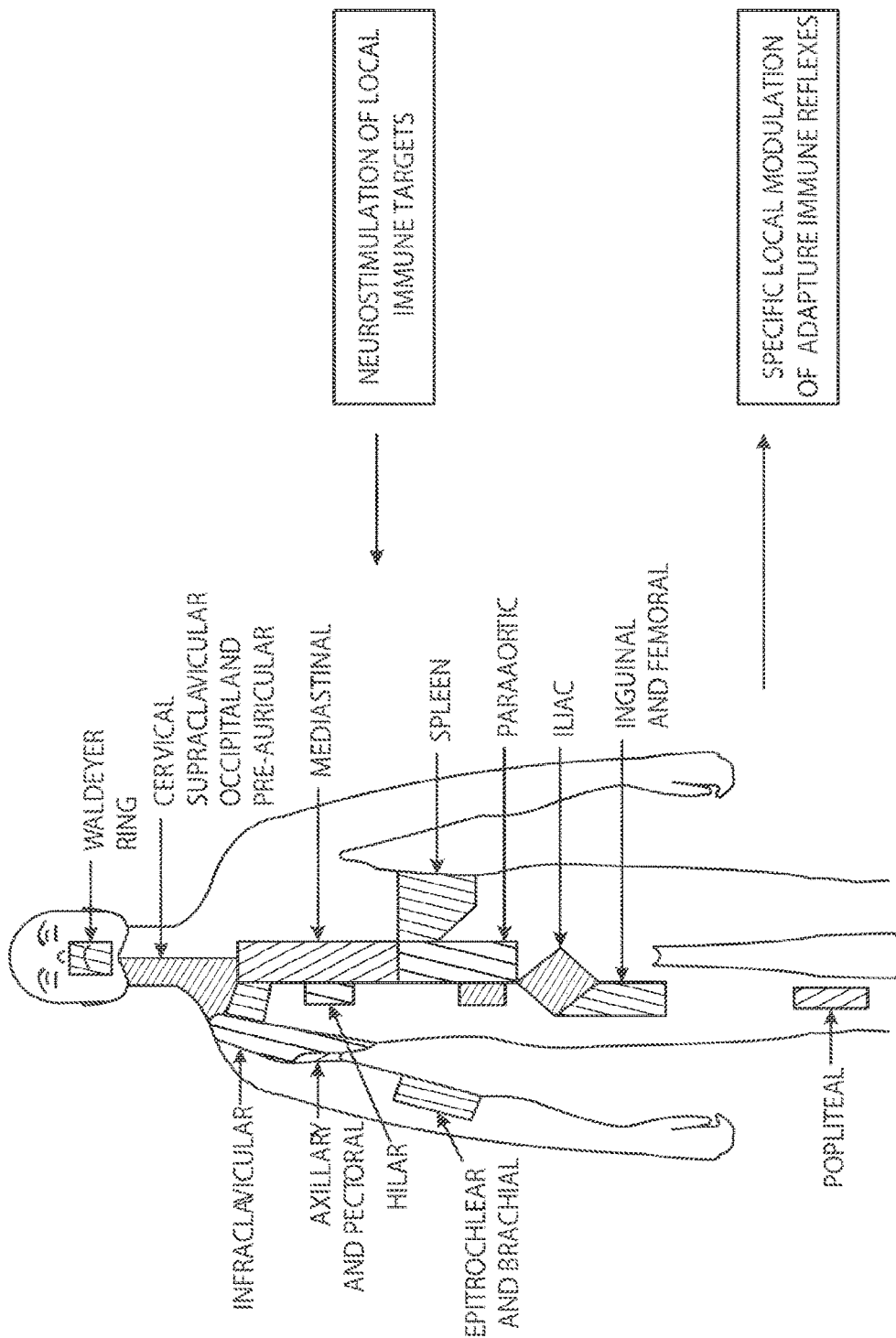
FIG. 11 shows an example of the different regions of lymphatic drainage, where specific lymph nodes are responsible for draining specific areas of the body.

FIG. 11 shows the known separation of the lymphatic system into multiple tissue draining segments. Neuromodulation of specific portions of the adaptive immune reflex may allow specific modulation of adaptive immune processes within local regions of the lymphatic system.

Figure 12:
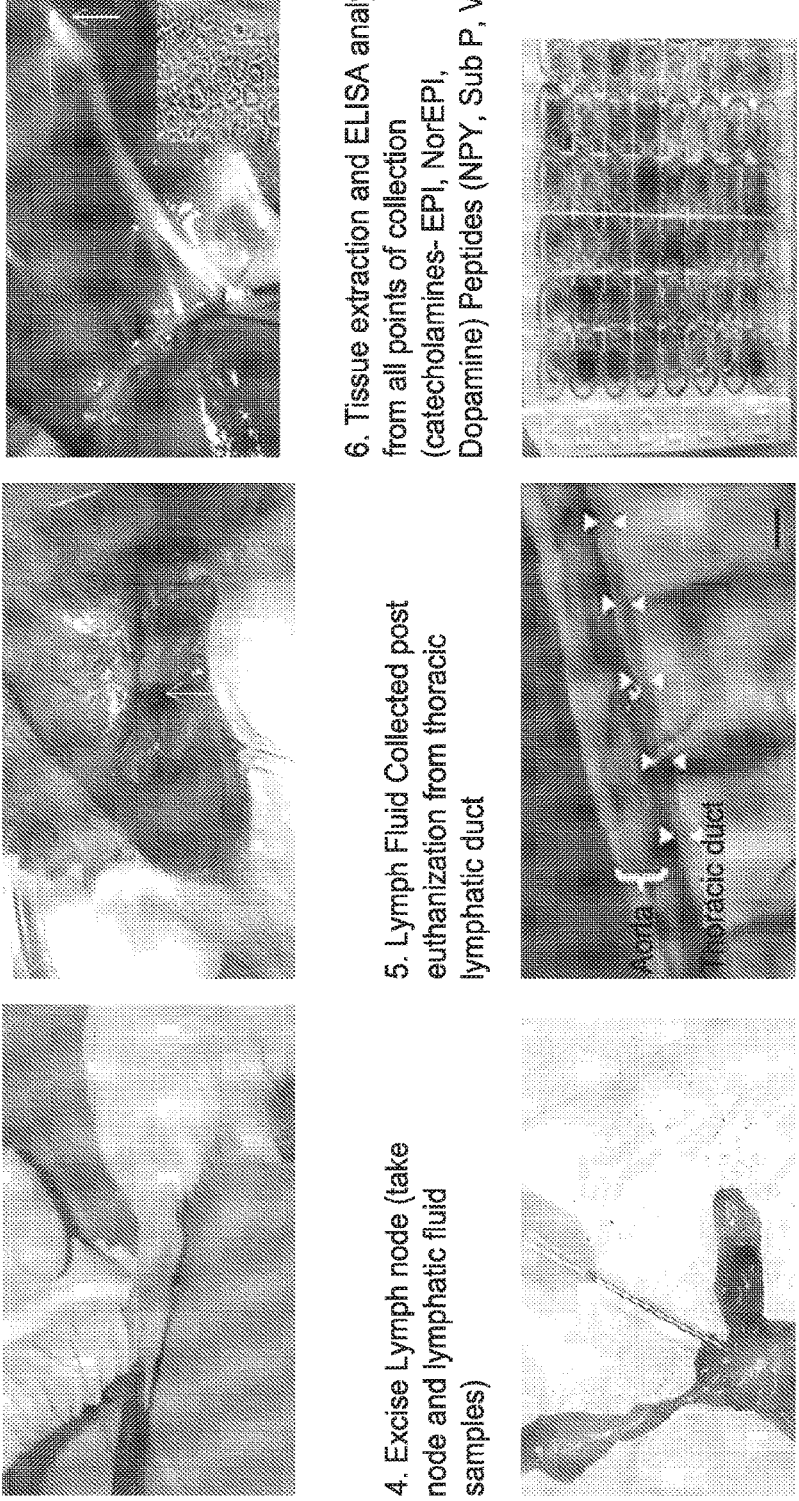
FIG. 12 shows the experimental process used to access the ability to differentially stimulate an adaptive immune reflex.

FIG. 12 depicts the standard experimental methods used to investigate differential stimulation or modulation of adaptive immune reflexes in one embodiment of the invention. Dye was first injected into the subject's foot pad, which causes dye to spread within the lymphatic system of the injected leg. This dye enabled visualization of both the lymph node (lymph node was not dissected itself in stimulation experiments) and the nerves innervating the chosen lymph node. The right popliteal lymph node was chosen for direct stimulation in one embodiment, and the sciatic nerve was chosen as the stimulation site directly above this lymph node. A bipolar insulated electrode was placed around the sciatic nerve at this site (one pole on each side of the nerve), and stimulation was achieved using a power supply and function generator attached to leads that contacted the two electrodes. After five minutes of stimulation the local lymph node was dissected (along with other nodes and tissue compartments), lymph fluid was collected via the lymphatic duct, and blood was collected from a large vein. The extracted tissue were processed and analyzed for either neurotransmitter concentrations (analyzed using HPLC or Elisa), neuropeptide concentrations (analyzed using Elisa), or total and specific immune cell counts (insert blood analyzer details; after further processing into a single cell suspension). Controls for these experiment included naïve (no stimulation), sham (electrode insertion but no stimulation), and neurectomy (nerve innervating the lymph node cut prior to stimulation) controls.

Lymphatic Tissue

The present techniques involve stimulation of immune cells and/or structures of the lymphatic system. As disclosed herein, the stimulation may affect functions of the lymph system, such as cell accumulation, drainage, cell proliferation, etc. The lymph system includes lymphatic organs, the lymph vessels that extend throughout the body and provide flow and drainage, and the lymph fluid that is transported within the lymphatic system. Lymph vessels transport immune cells from other tissues to the lymph nodes and lymphatic organs, such as the spleen and thymus. The lymphatic vessels are a network of vessels that carry lymph fluid and cells and that extend into tissues throughout the body. Primary lymph organs include the thymus and the bone marrow. The spleen, lymph nodes, Peyer's patches, and accessory lymphoid tissue (including the tonsils and appendix) are secondary lymphoid organs. These organs are made up of a scaffolding of connective tissue that supports circulating B- and T-lymphocytes and other immune cells, including, for example, macrophages, dendritic cells, and eosinophils. When microorganisms invade the body or the body encounters other antigens, the antigens are typically transported from the tissue to the lymph. The lymph is carried in the lymph vessels to regional lymph nodes. In the lymph nodes, the macrophages and dendritic cells phagocytose antigens, process antigens, and present antigens to lymphocytes, which can then start producing antibodies or serve as memory cells to recognize the antigens again in the future. Lymph and lymphoid tissue thus contain antibodies and immune cells. Lymphatic tissue consists of well-defined structural components including the cortex (e.g., mainly B-lymphocyte populated areas, including folliculus), the paracortex (e.g., mainly T-lymphocyte populated areas), and the lymphatic sinuses which are often surrounded by macrophage-populated areas.

Lymph nodes act as filters for lymph fluid carried via the lymph vessels and include internal compartments of lymphocytes to collect and destroy bacteria and viruses carried via the lymph vessels. Lymph nodes also produce lymphocytes and antibodies. When the body is fighting an infection, these lymphocytes multiply rapidly and produce a characteristic swelling of the lymph nodes. Approximately twenty-five billion different lymphocytes migrate through each lymph node every day. Lymph is transported to progressively larger lymphatic vessels culminating in the right lymphatic duct (for lymph from the right upper body) and the thoracic duct (for the rest of the body). These ducts drain into the circulatory system at the right and left subclavian veins, near the shoulders. Along the network of lymphatic vessels are a series of various lymphatic tissues and organs, including lymphatic nodules, Peyer's patches, tonsils, lymph nodes, the thymus, and the spleen. Lymph nodes encapsulate many lymphatic nodules within a tough capsule and are supplied with blood vessels and lymphatics. Lymph nodes filter the lymph delivered to them by lymphatic vessels.

Thus, lymph nodes filter the lymph draining from the lymphatic capillary bed in which the lymph node is situated.

Clusters of lymph nodes are found in various anatomical regions and the methods of the present invention may be used for the localized neuromodulation of one or more of these lymphatic regions. For example, clusters of lymph nodes are found in the underarm (the axillary lymph nodes), the groin (the inguinal lymph nodes), the neck (the cervical lymph nodes), the chest (pectoral lymph nodes), and the abdomen (the iliac lymph nodes). Other lymphatic clusters include, but are not limited to, the popliteal lymph nodes, parasternal lymph nodes, lateral aortic lymph nodes, paraaortic lymph nodes, submental lymph nodes, parotid lymph nodes, submandibular lymph nodes, intercostal lymph nodes, diaphragmatic lymph nodes, pancreatic lymph nodes, citerna chili, lumbar lymph nodes, sacral lymph nodes, obturator lymph nodes, mesenteric lymph nodes, mesocolic lymph nodes, gastric lymph nodes, hepatic lymph nodes, and splenic lymph nodes. The disclosed techniques may be used for direct neuromodulation of nerves that innervate any one or more of these lymphatic regions.

Neural Modulation

The human nervous system is a complex network of nerve cells, or neurons, found centrally in the brain and spinal cord and peripherally in the various nerves of the body. Neurons have a cell body, dendrites and an axon and axon terminal that contains the synapse and from which neurotransmitters are released. A nerve is a group of neurons that serve a particular part of the body. Nerves may contain several hundred neurons to several hundred thousand neurons. Nerves often contain both afferent and efferent neurons. Afferent neurons carry signals back to the central nervous system and efferent neurons carry signals to the periphery. A group of neuronal cell bodies in one location is known as a ganglion. Electrical signals are conducted via neurons and nerves. Neurons release neurotransmitters at synapses (connections) with other nerves to allow continuation and modulation of the electrical signal. In the periphery, synaptic transmission often occurs at ganglia.

The electrical signal of a neuron is known as an action potential. Action potentials are initiated when a voltage potential across the cell membrane exceeds a certain threshold. This action potential is then propagated down the length of the neuron. The action potential of a nerve is complex and represents the sum of action potentials of the individual neurons in it. Myelinated neurons (and nerves) conduct electricity in a saltatory manner with the exception of the nodes of Ranvier. Without this saltatory conduction, electrical signal propagation would be considerably slower (e.g. 2 m/s in an unmyelinated vs. 200 m/s in a myelinated nerve)

The system provided herein may provide energy pulses according to various stimulation parameters. For example, the stimulation parameters may include various stimulation time patterns, ranging from continuous to intermittent. Energy is delivered for a period of time at a certain frequency (e.g., 0.5 Hz-30 KHz or, in certain embodiments, 0.5 Hz-200 Hz) during the signal-on time. The signal-on time is followed by a period of time with no energy delivery, referred to as signal-off time. The neural modulation pattern may comprise various combinations of pulse width (the duration of a single pulse) and frequency (the interval between neighboring pulses). The neuromodulation pattern may be determined based on empirical evidence, e.g., based on patient data from previously treated patients, and/or may be customized for a particular patient. For example, the modulation pattern may be selected based on patterns determined to be successful for patients have similar clinical conditions that were successfully treated. The modulation patterns may also be selected based on recording of nerve activity in the patient to determine successful modulation and/or tracking of downstream effects of modulation (e.g., neuropeptide or neurotransmitter concentration or other characteristics as provided herein).

The treatment duration may last for as little as a few minutes to as long as several hours. Treatment duration with a specified stimulation pattern may last for one hour. Pulse generation for nerve modulation is accomplished using a pulse generator. Pulse generators can use conventional microprocessors and other standard electrical components. The stimulation parameters may also include frequency, duration, pulse shape, current, or voltage parameters. A pulse generator for this embodiment can generate a pulse, or energy signal, at frequencies ranging from approximately 0.5 Hz to 30 KHz, a pulse width from approximately 10 to 1,000 microseconds, and a constant current of between approximately 0.1 milliamperes to 20 milliamperes. The pulse generator may be capable of producing a ramped, or sloped, rise in the current amplitude. In another embodiment, the pulse generator is a voltage generator that produces a constant voltage in a range of 0.5V-10V. The pulse generator may, in certain embodiments, communicate with an external controller and/or monitor.

Bipolar stimulation of a nerve can be accomplished with multiple electrode assemblies with one electrode serving as a positive node and the other serving as a negative node. In this manner nerve activation can be directed primarily in one direction (unilateral), such as efferently, or away from the central nervous system. Unipolar stimulation can also be performed. As used herein, unipolar stimulation includes a single electrode on the lead, while an implanted pulse generator itself, or a ground electrode essentially functions as a second electrode, remote from the lead electrode. With unipolar stimulation, a larger energy field is created in order to electrically couple the electrode on the lead with the remote electrode. This allows successful nerve stimulation with a single electrode placed only in "general proximity" to the nerve, meaning that there can be significantly greater separation between the electrode and the nerve than the "close proximity" required for bipolar stimulation. The magnitude of the allowable separation between the electrode and the nerve will necessarily depend upon the actual magnitude of the energy field which the operator generates with the lead electrode in order to couple with the remote electrode.

The techniques provided herein may include stimulation of one or more lymphatic tissue. In addition, insofar as a lymphatic tissue is innervated by a plurality of nerves, the stimulation may involve one or more nerves. For example, the electrode may be positioned to deliver energy within a tissue area that affects multiple nerves.

Lymph Node Innervation

Provided herein are techniques to modulate neural pathways to produce a therapeutic outcome. Modulation may take place through direct electrical stimulation of the nerve/neural pathway (i.e. an implanted stimulation device with electrode) or through non-invasive means (i.e. eliciting action potentials or neural activity by passing energy to the nerve from outside the body, which may be in several forms including a magnetic field, an external electrical field, or ultrasonic wave). The neural pathways to the lymph node also may be modulated using these stimulation techniques. That is, the stimulation may be targeted to an upstream or downstream nerve location that is not within or adjacent to lymphatic tissue but that is part of the neural pathway to or from the lymphatic tissue.

Lymphatic tissue may be innervated by nerves of the peripheral nervous system, which includes sensory and motor nerves. Such nerves may include nerves of the autonomic nervous system, which carries signals to glands, cardiac muscle, and smooth muscle and which can be further divided into the sympathetic and parasympathetic divisions. An adrenergic nerve fiber releases the neurotransmitter, e.g., adrenaline (epinephrine), noradrenaline, or dopamine. These neurotransmitters are released at the synapse, which is a junction point between the axon of one nerve cell and the dendrite of another (or junction point/synapse with a non-nerve cell). Sympathetic noradrenergic nerve fibers innervate certain lymph tissues and generally are directed into zones of T lymphocytes and plasma cells rather than into nodular regions or B lymphocyte regions. For example, in the thymus, noradrenergic fibers enter with nerve bundles and plexuses around blood vessels. In the spleen, noradrenergic fibers enter with the vasculature and are distributed mainly in the white pulp along the central artery and associated periarterial lymphatic sheath. Fibers branch from a dense plexus around the central artery and travel into the parenchyma, where they end among fields of lymphocytes and other cell types. In lymph nodes, noradrenergic fibers enter at the hilus, travel along the vasculature and in a subcapsular plexus, and branch into the parenchyma in paracortical and cortical regions, where they end among lymphocytes. In the gut, sacculus rotundus, and Peyer's patches, noradrenergic fibers enter at the serosal surface, travel longitudinally with the muscularis interna, turn radially into internodular plexuses, plunge directly through the thymus-dependent zones, and ramify profusely among lymphocytes, enterochromaffin cells, and plasma cells in the interdomal regions. In the bone marrow, noradrenergic fibers enter with blood vessels, distribute deeply into the marrow on those vessels, and branch sparsely into the substance of the marrow. Other types of nerve fibers that may be found include peptidergic fibers. The effects of neuromodulation may be affected by the type of nerve fiber that is stimulated.

Therapeutic Benefits of Lymphatic Tissue Stimulation

Many diseases are caused by or exacerbated by a defect in immune system signaling. These include auto-immune disease (in which immune cells become activated against self-antigen), inflammatory disease (in which immune cells are chronically held in a destructive or active state), and cancers (in which tumors may develop a protective immune cell profile, eliminating the ability of the immune system to attack the abnormal or cancerous cells). Control points for many of these processes exist in the lymph node. Circulating immune cells often enter lymph nodes (either passively or through active/targeted processes) and receive signals/commands that differ from the surrounding tissue and blood. Other immune cells (and supporting cells) reside in the lymph node and continually secrete signals into the blood stream to effect cells outside of the lymph compartment. As discussed above, neural stimulation and control of either of these immune cell populations may be used to treat a number of diseases. Electrical activation of the post-synaptic sympathetic neurons results in the release of catecholamines (epinephrine, norepinephrine, dopamine). Peptidergic neurons may also release peptide-based neurotransmitters, such as NPY, substance P, and VIP. Parasympathetic nerve fibers may release other neurotransmitters, such as acetylcholine. As provided herein, the neuromodulation techniques may be used to treat a subject with one of the diseases or conditions provided herein. However, it should be understood that the examples are non-limiting, and the techniques may be used to treat any subject in need of an alteration of immune function.

As provided herein, neuromodulation of lymphatic tissue may result in immunomodulation and/or changes in activity or function of lymphatic tissue. It should be understood that certain therapeutic outcomes may be associated with blocking effects while other therapeutic outcomes may be associated with an increase in lymphatic activity. In certain embodiments, neuromodulation of a lymph node results in local enlargement of the lymph node relative to a contralateral lymph node. The enlargement, or hypertrophy, may be associated with a change in peri-lymphatic vessel muscle cell tone, longer term recruitment and re-organization of lymphatic vessels around the lymph node, and/or molecular changes at key barrier tissues (such as high endothelial venules (HEV) within the lymph node) including alteration of important transport proteins (such as aquaporin (water/liquid transport), or CCL21/CXCL13 secretion (cell chemokines)). The changes may result in dramatic shifts in cell densities, cell counts, and the overall lymph node tissue environment, including the enlargement. Further, activation of the lymph node may result in an activation chain that expands or amplifies the local activation to systemically activate the lymphatic system. That is, local stimulation may result in downstream and upstream activation of lymphatic systems. Accordingly, local neuromodulation may be used to activate a systemic immune response. Such activation may be beneficial for subjects with conditions associated with faulty or decreased immune responses. Such activation may also enhance the body's own response to fighting pathogens. Accordingly, neuromodulation may be used to achieve alteration of lymphatic fluid flow, immune cell trafficking into/out of the lymphatic tissue, alteration of immune cell phenotype or local immune response, and/or antigen trafficking into/out of the lymphatic tissue. Local stimulation may enable tissue or location specific increase in lymphatic fluid or immune cell recruitment.

Lymphatic tissue neuromodulation may be used to change the population of immune cells produced by lymphatic structures. In one embodiment, neuromodulation of the lymph nodes may result in an increase in the population of lymphocytes circulating in the lymphatic fluid. Neuromodulation of a lymph node modulates the local concentration profile of type 1 (pro-inflammatory) cytokines (e.g. IL-12, TNF-alpha, IFN-gamma, IL-2, TNF-beta) and type 2 (anti-inflammatory) cytokines (e.g. IL-4, IL-10, IL-13, IL-6). Such modulation could occur through the release of norepinephrine from the nerves of the lymphoid organ and its corresponding binding to beta adrenergic receptor of T cells. In one embodiment, neuromodulation of the lymph nodes may result in an increase or decrease in B or T cells circulating on the lymphatic fluid, or an increase or decrease in B or T cells or dendritic cells recruited into lymphatic tissue. Accordingly, neuromodulation of lymphatic tissue may result in a chance in cell migration patterns. Such migration patterns may be observed using in vivo bioluminescence imaging.

The subject's condition may be used to select the appropriate lymph structure or structures for neuromodulation. For example, occipital, auricular, cervical, axillary, or epitrochlear nodes tend to be enlarged in response to particular pathogens, while other lymph nodes, such as the inguinal, pulmonary, mediastinal, intraabdominal nodes, may be more likely to have pathologies associated with carcinoma or lymphomas.

In another embodiment, neuromodulation may be used to affect the lymphatic drainage or flow. For example, stimulation using particular parameters may increase local and/or systemic lymphatic drainage, which in turn may enhance the resolution of an immune response. In one implementation, neuromodulation may enhance wound healing by enhancing drainage of pathogens away from the site of a wound and recruitment of additional immune cells to fight infection. The modulation of interstitial fluid flows in tumors or diseased tissues through neuromodulation of downstream lymphatics might also be used to improve target delivery and localized concentrations of pharmaceuticals. In yet another embodiment, neuromodulation at blocking frequencies (e.g., greater than 1000 Hz) or voltages may be used to decrease neuronal input to the lymphatic tissue.

An increase in drainage may also provide benefits to subjects with disorders of lymph circulation, such as lymphedema, such as a decrease in swelling of the limbs. Lymphatic flow is modulated by interstitial fluid pressures at the sites of initial lymphatic capillaries, one way valves of the lymphatic vessels, and nerves and hormones that control contractions of smooth muscle cells of lymphatic vessels and lymphangion structures. Neuromodulation may activate a local muscle contractile response in addition to releasing neurotransmitters that amplify an autonomic regulatory response to increase lymphatic flow. For a subject with cancer, a decrease in lymphatic drainage/flow rate, or cell transport within the lymphatic system may help decrease the possibility of metastases. Such blocking parameters may include relatively higher stimulating voltages or frequencies relative to activating voltages or frequencies.

Assessing Lymphatic Tissue Function

The disclosed techniques may be used for lymphatic function assessment. The disclosed techniques may use direct assessments of lymphatic condition or function. For example, for a subject in need of increase lymphatic drainage, such drainage may be monitored before, during and/or after stimulation to determine if the selected parameters have achieved a sufficient increase. Accordingly, lymphatic drainage may be assessed by one or more in vivo techniques that determine lymphatic drainage. In one embodiment, an exogenous contrast agent is administered either directly into the lymphatic tissue or indirectly via intradermal injection. For example, a gadolinium-based contrast media may be used. Either local or systemic flow may be addressed, depending on the desired clinical outcome. For example, MR lymphangiography may be used to assess lymphatic drainage in the limbs. However, MR imaging may be challenging for the case of a subject with an implantable electrode.

In another embodiment, fluorescence microlymphangiography (FML) may also be used to assess lymphatic drainage. FML employs the intradermal administration of a fluorescent dye, FITC conjugated to dextran (FITC-dextran), and video fluorescence microscopy techniques to acquire high-resolution images. In another embodiment, quantum-dot optical lymphatic imaging may be used for in vivo lymphatic imaging and lymphatic flow assessment. In yet another embodiment, imaging may include dyes or indicators that target lymph-specific markers, such as LYVE-1, Prox-1, podoplanin, and VEGFR3.

The images from the assessment techniques may be received by the system for automatic or manual assessment. Based on the image data, the stimulation parameters may also be modified. In one embodiment, the assessment parameter is a relative change in size or estimated volume of the stimulated lymphatic tissue. For example, if the image data shows an increase in size of the lymph node above a threshold (e.g., an increase of at least 25%, or 50% in estimated volume relative to the unstimulated state), the stimulation may be considered to be successful and the parameters may be unmodified or may be stepped back to the lowest energy that achieves a desired outcome. Further, the increase in size may be assessed within a pre-defined time window (e.g., within 5-10 minutes after the start of the modulation). Similarly, if the lymphatic drainage has increased in the presence of stable vital signs and other health indicators, the stimulation frequency or voltage may be stepped back to the lowest energy that achieves a desired outcome, e.g., maintains the desired elevated lymphatic drainage. In other embodiments, the change in lymphatic drainage or size is utilized as a marker of local neurotransmitter concentration, and used as a surrogate marker for exposure of local immune (immune interacting) cells to phenotype modulating neurotransmitters, and effectively a marker of the predicted effect on immune function.

Additionally or alternatively, the system may assess the presence or concentration of neurotransmitters or cells in the lymph tissue or lymphatic fluid. Lymphatic fluid or tissue may be acquired by a fine needle aspirate, and the assessment of the presence or levels of neurotransmitters (e.g., peptide transmitters, catecholamines) may be performed by any suitable technique. Analysis of secondary signaling molecules may also be useful, including inflammatory molecules and cytokines (i.e. TNF-alpha or IL6), whose secretion from local immune cells may be effected by neuromodulation.

In another embodiment, a change in the types and/or numbers of cells in the lymph node or lymphatic tissue may be an indication of lymphatic tissue function. The cell population may be assessed by ex vivo techniques, such flow cytometry. In another example, the lymphatic cell population may be assessed by laser-scanning in vivo confocal microscopy (IVCM) using endogenous contrast. In cases where lymph enlargement is mediated by cell entry into the lymph node, relative increases in cell populations may also be indicative of such cell entry. Cell recruitment and migration in lymph nodes is assessed by measuring changes in size of the lymph nodes; size may be assessed using sonography, cross-sectional CT or MRI. These imaging analyses may include morphological criteria to capture neuromodulation-induced changes in lymph node structure. As mentioned, contrast-enhanced MRI may be used. The contrast agent may be used dynamically, where enhancement or decrease in the kinetics of contrast agent movement may denote microcirculatory changes associated with neuromodulation (such as blood/lymph volume, microvascular permeability, or increased fractional volume of the extracellular space within the lymphatic tissue). Nanoparticle-enhanced MRI may also provide a method of evaluating neuromodulation of lymphatic tissue. For example, ferumotran-10 is known to enter lymph tissue and bind to macrophages, producing decreased signal intensity on T2- and T2*-weighted images (image characteristics dependent on cell density and tissue size). PET may be used in analysis of neuromodulation effect on lymphatic tissue; F-FDG uptake may denote increased glucose utilization in immune cells affected by the neural stimulus. Other newer imaging agents may be useful in analyzing neuro stimulation induced lymph node alterations, including near-infrared fluorescent probes which have recently been used to visualize lymph nodes in animals after intravenous (pan-node) or subcutaneous (local node) administration.

Examples

Figure 13:
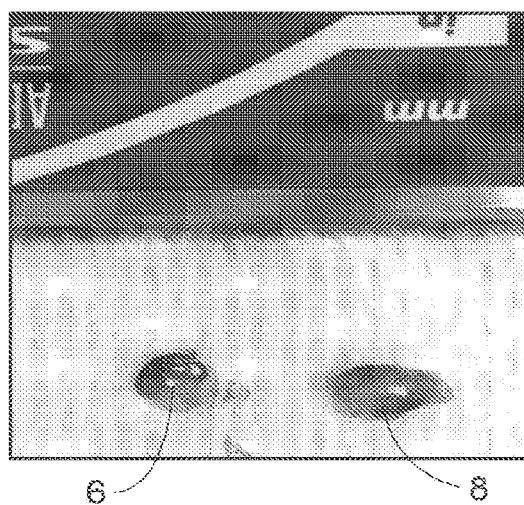
FIG. 13 shows an image of the excised popliteal lymph node on the stimulated leg and the contralateral/non-stimulated leg.

Direct stimulation was performed on animal subjects and stimulation data was collected from neurotransmitters and three neuropeptides (with and without stimulation) from both the lymph node tissue and lymph fluid drained from the node. FIG. 13 depicts popliteal lymph nodes on the right (stimulated) leg and left (unstimulated leg) after stimulation. The stimulated lymph node (8) appeared larger in each subject compared to the "unstimulated" lymph node (6). In addition, the stimulated lymph was shown to increase in overall weight compared to the unstimulated lymph node, as shown in FIG. 14.

Figure 14:
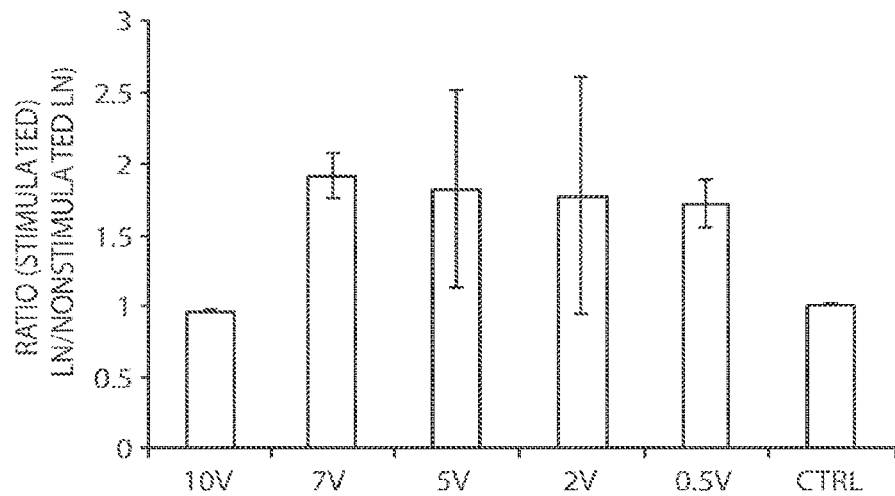
FIG. 14 shows the results of a comparison of the weight of stimulated vs. nonstimulated popliteal lymph nodes.

FIG. 14 shows the results from a comparison of stimulated vs. unstimulated lymph nodes for different subject groups after stimulation of a popliteal lymph node and across different stimulating voltages. For each subject, the stimulated popliteal lymph node and the unstimulated contralateral lymph node were removed after stimulation and the ratio of the weights of the lymph nodes for each individual subject was determined. In the control, the weights of the stimulated and unstimulated lymph nodes were similar, with a ratio of 1. At certain stimulation voltages (0.5V, 2V, 5V, and 7V), the stimulated lymph node was almost double the weight of the unstimulated lymph node. At even higher voltages (10V), the effect was not observed. The observed hypertrophy of the stimulated lymph node may be associated with increased lymphatic activity, such an increased in liquid flux into the extracellular space of the lymphatic tissue, or an increased cellularity due to immune cell recruitment in the stimulated lymph node.

Figure 15A:
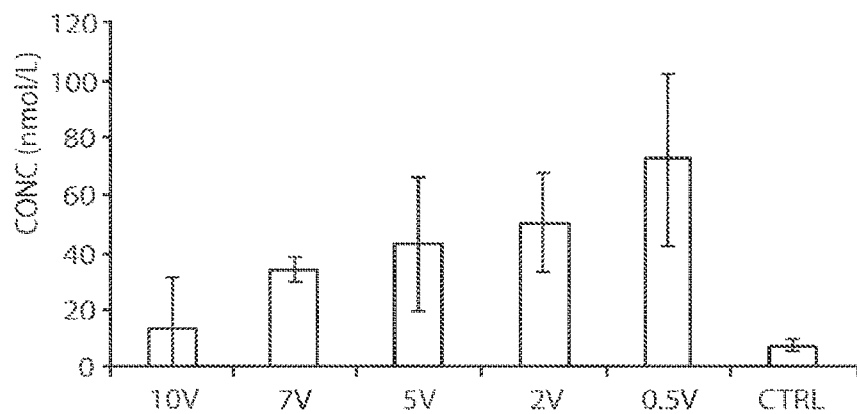
FIG. 15A shows the concentration of epinephrine in the popliteal lymph node (stimulated leg) after stimulation at different voltages.
Figure 15B:
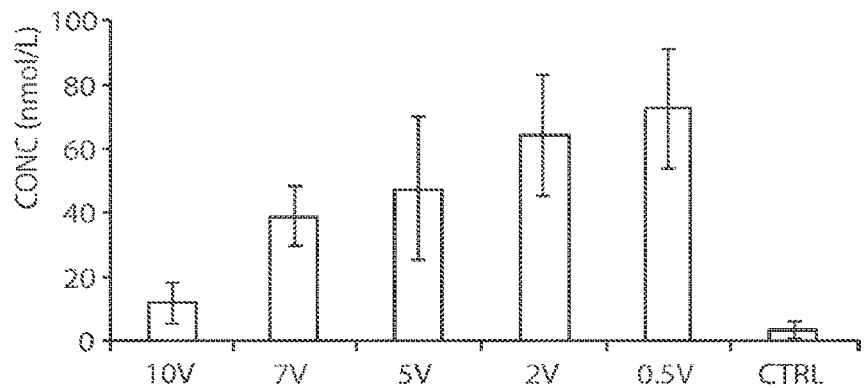
FIG. 15B shows the concentration of epinephrine in lymphatic fluid after stimulation at different voltages.

Studies were also performed to examine the effect of neuromodulation on the release of various neurotransmitters, in both the lymph node and lymphatic fluid after stimulation, with treatment groups of N=5-8. FIG. 15A shows the concentration of epinephrine in the popliteal lymph node after stimulation at different voltages and FIG. 15B shows the concentration of epinephrine in lymphatic fluid after stimulation at different voltages. A significant increase was observed for certain stimulation voltages (0.5V, 2V, 5V, and 7V) while the effect was less pronounced at higher voltages (10V). Stimulation at 0.5V, for example, resulted in a greater than 20-fold increase in epinephrine concentrations in both the lymph node and lymphatic fluid.

Figure 16A:
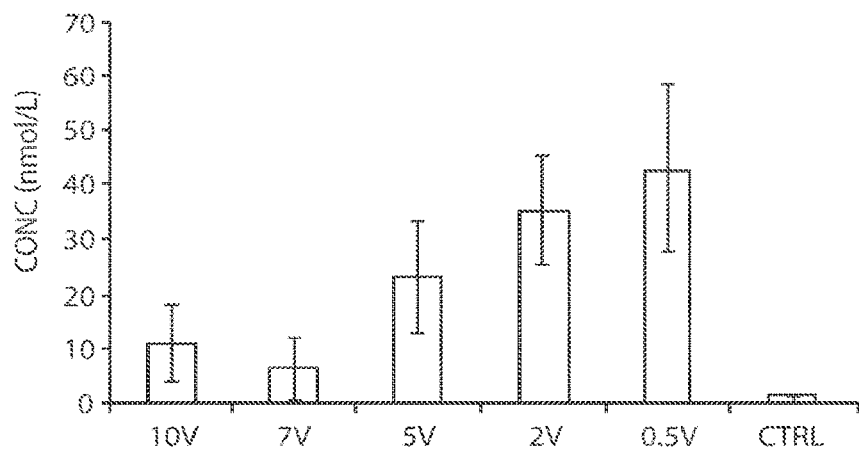
FIG. 16A shows the concentration of norepinephrine in the popliteal lymph node after stimulation at different voltages.
Figure 16B:
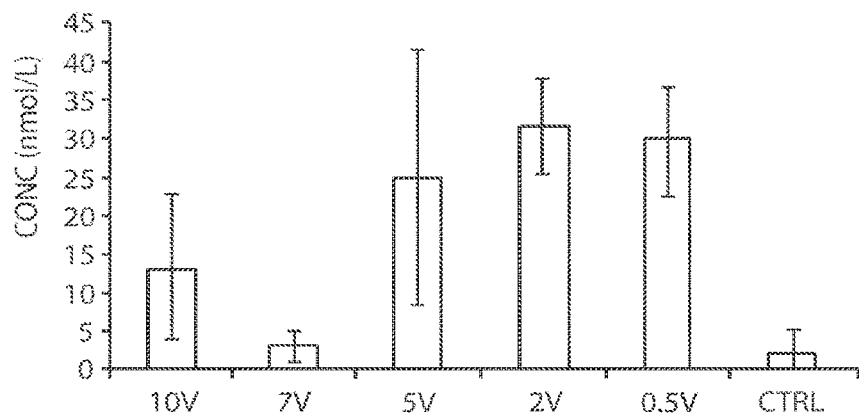
FIG. 16B shows the concentration of norepinephrine in lymphatic fluid after stimulation at different voltages.

FIG. 16A shows the concentration of norepinephrine in the popliteal lymph node after stimulation at different voltages and FIG. 16B shows the concentration of norepinephrine in lymphatic fluid after stimulation at different voltages. For norepinephrine, a similar increase in release was observed in response to the stimulation. Based on the observed samples, the effect dropped off at higher (10V) stimulation voltages.

Figure 17A:
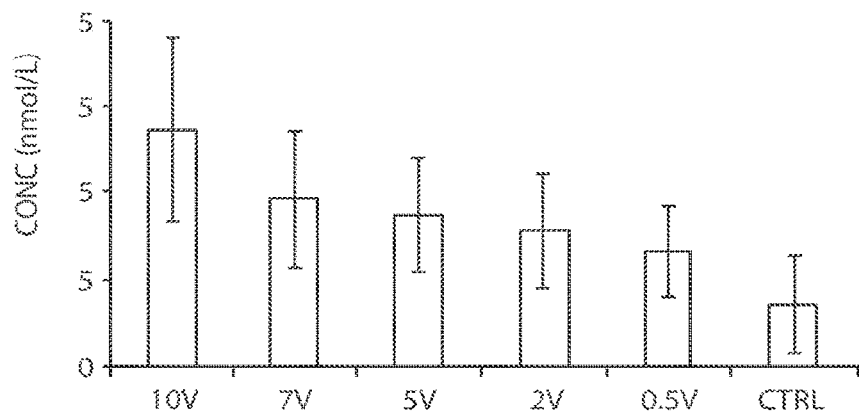
FIG. 17A shows the concentration of dopamine in the popliteal lymph node after stimulation at different voltages.
Figure 17B:
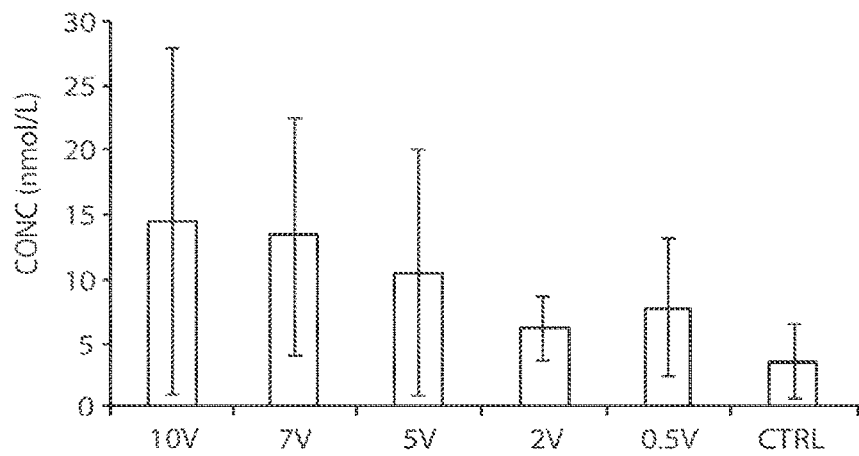
FIG. 17B shows the concentration of dopamine in lymphatic fluid after stimulation at different voltages.

FIG. 17A shows the concentration of dopamine in the popliteal lymph node after stimulation at different voltages and FIG. 17B shows the concentration of dopamine in lymphatic fluid after stimulation at different voltages. Overall, dopamine showed an opposite trend (higher levels at larger applied voltage), and for most of the applied voltage dopamine concentrations were not significantly different than controls.

Figure 18A:
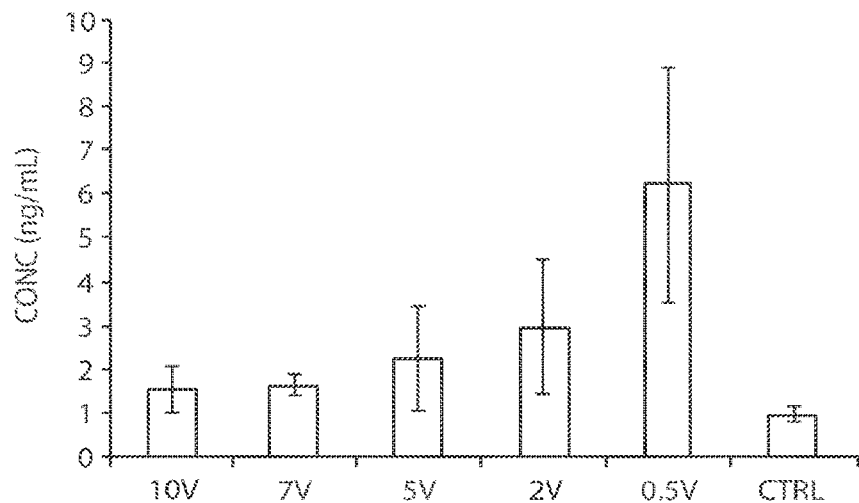
FIG. 18A shows the concentration of neuropeptide Y in the popliteal lymph node after stimulation at different voltages.
Figure 18B:
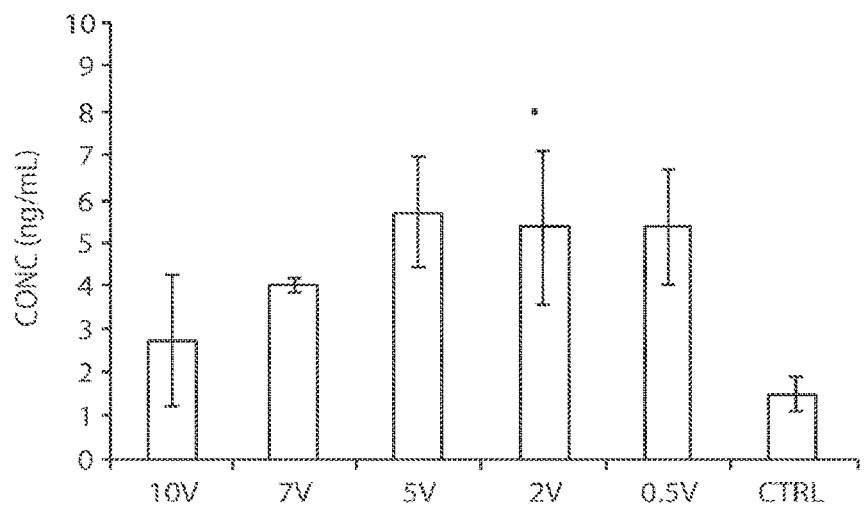
FIG. 18B shows the concentration of neuropeptide Y in lymphatic fluid after stimulation at different voltages.
Figure 19A:
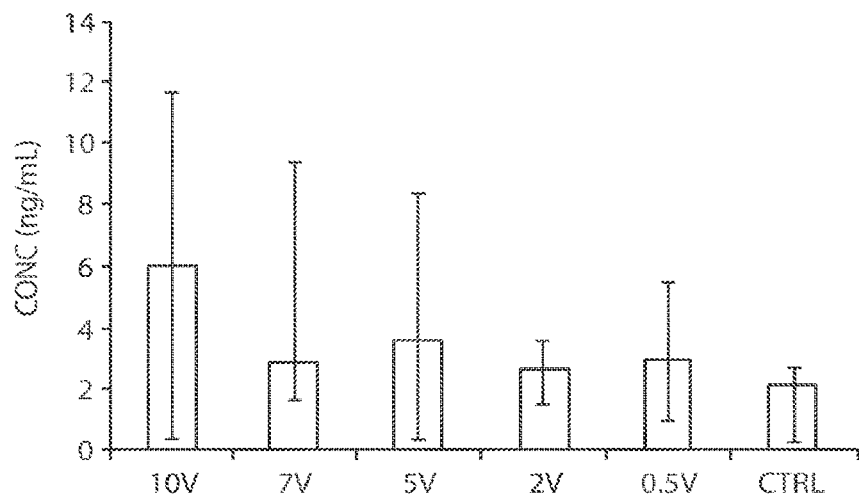
FIG. 19A shows the concentration of substance P in the popliteal lymph node after stimulation at different voltages.
Figure 19B:
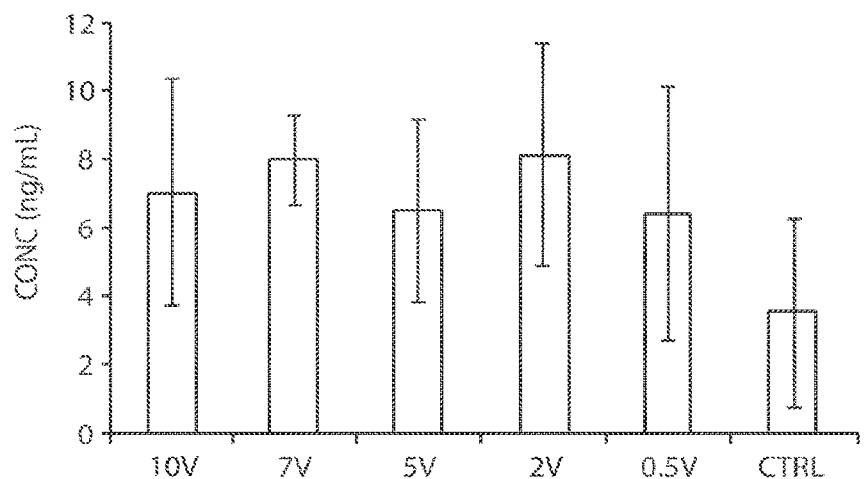
FIG. 19B shows the concentration of substance P in lymphatic fluid after stimulation at different voltages.
Figure 20A:
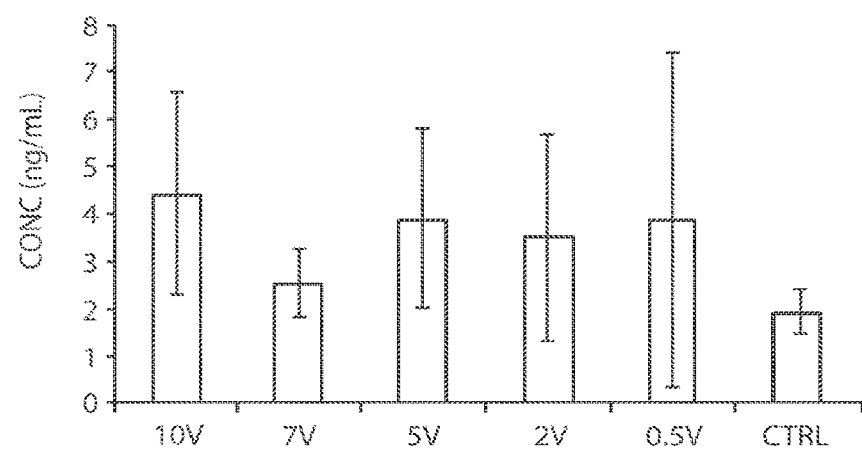
FIG. 20A shows the concentration of vasoactive intestinal peptide in the popliteal lymph node after stimulation at different voltages.
Figure 20B:
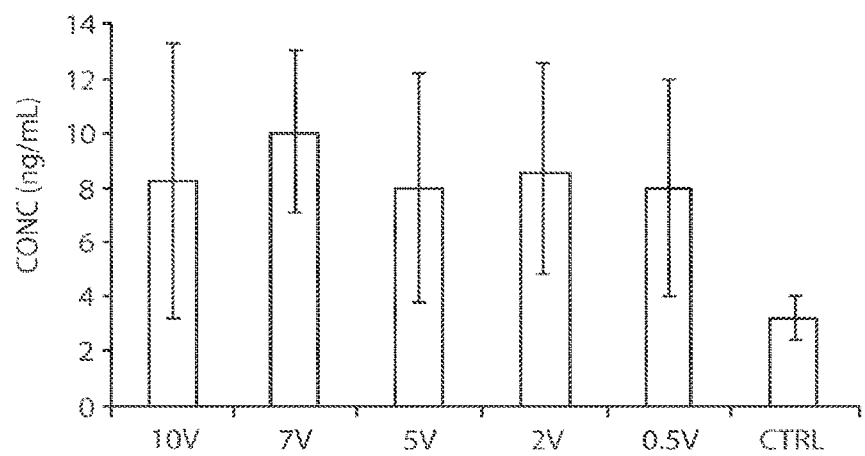
FIG. 20B shows the concentration of vasoactive intestinal peptide in lymphatic fluid after stimulation at different voltages.

The effect of neuromodulation on peptide transmitter was also observed. FIG. 18A shows the concentration of neuropeptide Y in the popliteal lymph node after stimulation at different voltages and FIG. 18B shows the concentration of neuropeptide Y in lymphatic fluid after stimulation at different voltages. FIG. 19A shows the concentration of substance P in the popliteal lymph node after stimulation at different voltages and FIG. 19B shows the concentration of substance P in lymphatic fluid after stimulation at different voltages. Substance P did not show a significant increase in the lymph node, but was slightly elevated relative to the control in the lymphatic fluid for certain stimulating voltages. FIG. 20A shows the concentration of vasoactive intestinal peptide in the popliteal lymph node after stimulation at different voltages and FIG. 20B shows the concentration of vasoactive intestinal peptide in lymphatic fluid after stimulation at different voltages. It should be noted that stimulation of extreme frequencies (i.e. 30 kHz) appear to have blocked the release of some neurotransmitters/neuropeptides.

Figure 21:
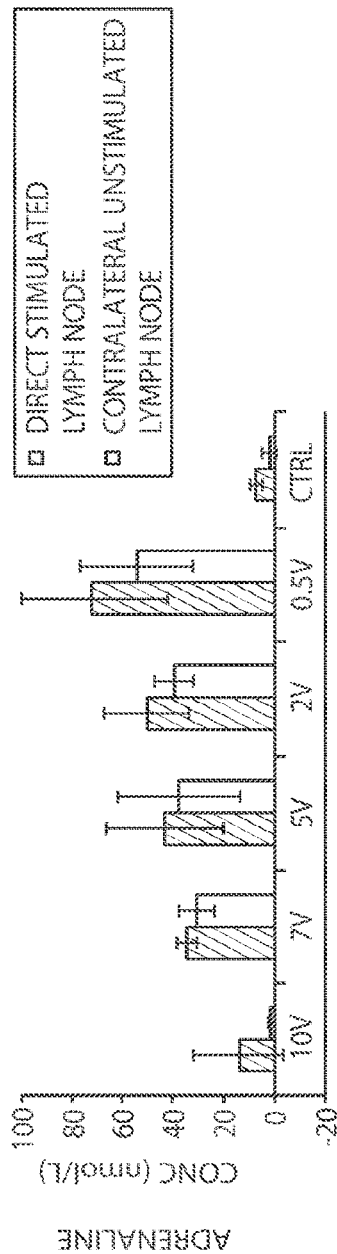
FIG. 21 shows a comparison of adrenaline concentration for a stimulated lymph node and an unstimulated contralateral lymph node in the same subject.
Figure 22:
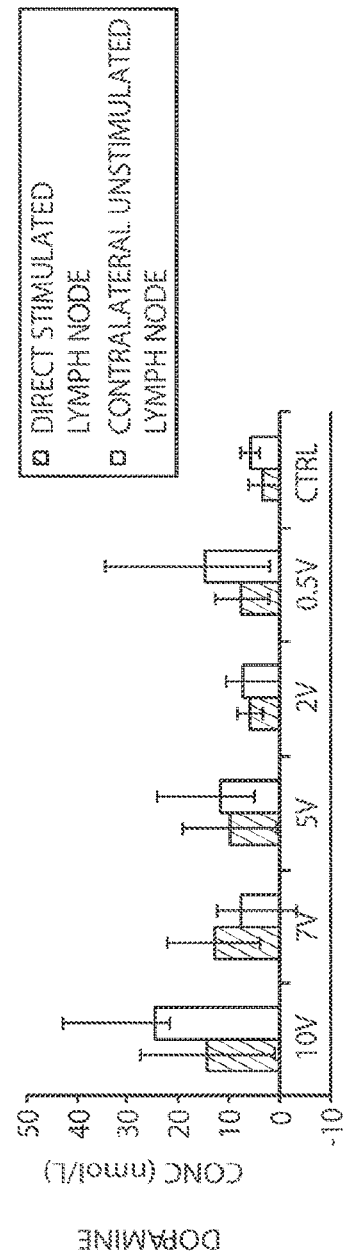
FIG. 22 shows a comparison of dopamine concentration with for a stimulated lymph node and an unstimulated contralateral lymph node in the same subject.

FIG. 21 shows a comparison of adrenaline concentration for a stimulated lymph node and an unstimulated (or contralateral left popliteal) lymph node in the same subject. One observed result is that stimulation appeared to create a contralateral stimulation effect. For example, at certain voltages tested (0.5V, 2V, 5V, and 7V), the contralateral lymph node was stimulated to release adrenaline significantly more the control. This points to a possible upstream and/or downstream connectivity. For example, stimulation that generates increased local lymphatic activity may result in the release of signals (e.g., neurotransmitters) that circulate through the lymphatic system and in turn activate the contralateral lymph node. Such activation may also provide central nervous system or peripheral nervous system activation, which in turn may serve to further amplify the local activation effects through a neural connection or reflex. FIG. 22 shows a comparison of dopamine concentration for a stimulated lymph node and an unstimulated contralateral lymph node in the same subject. For dopamine, the contralateral effect had little change over control, as observed on the stimulated lymph node. While these initial results do not shed light on the means of connectivity between the stimulated and contralateral side, it should be noted that the differential increase in size between the stimulated and contralateral lymph cannot be explained by the neurotransmitter measurements (as no differential effect is observed). To examine the effects of the nerve chain activation in contributing to the lymphatic function, a series of control studies were performed to examine stimulation on an intact nerve and a severed nerve relative to an intact, unstimulated control. The severed nerve, being unable to complete neural signaling through direct neural pathways to the lymph node, provided a control for the intact nerve experiments.

FIGS. 23A-F show concentrations of various neurotransmitters in lymph tissue for a stimulated lymph node with an intact nerve, a stimulated lymph node with a severed nerve, and a control. For epinephrine (FIG. 23A) and norepinephrine (FIG. 23B), the intact nerve demonstrated significantly greater neurotransmitter release relative to both the control and the severed nerve. Dopamine levels (FIG. 23C) were elevated in the control relative to the control and severed nerve. The effect was observed to a lesser degree with neuropeptide Y (FIG. 23D). Substance P levels showed the only opposite effect (FIG. 23E) in which levels were highest for the severed nerve, which may be the result of trauma-mediated release. VIP levels were relatively unchanged between the samples (FIG. 23F). In general these results demonstrate that changes in lymph node neurotransmitter and/or neuropeptide concentrations may be attributable to excitation/stimulation of a neural pathway.

In addition to examining the effects of stimulating voltage on lymphatic activity, various stimulating frequencies were also tested. FIGS. 24A-F show concentrations of various catecholamine neurotransmitters in lymph tissue at different stimulation frequencies. The largest effects were seen with epinephrine (FIG. 24A lymph node, FIG. 24D lymph fluid) and norepinephrine (FIG. 24B lymph node, FIG. 24E lymph fluid), which had the largest change relative to the control, and whose peak concentrations in both lymphatic tissue and lymphatic fluid were observed after stimulation at 20 Hz. For norepinephrine, stimulation at 20 Hz appeared to generate a significantly greater increase in release relative to other frequencies. For the three examined neurotransmitters, stimulation at 30 KHz appeared to be associated with a lack of neurotransmitter release. Results for dopamine are shown in FIG. 24C (lymph node) and FIG. 24F (lymph fluid). FIGS. 25A-F shows concentrations of various peptide neurotransmitters in lymph tissue at different stimulation frequencies. Results for neural peptide Y are shown in FIG. 25A (lymph node) and 25D (lymph fluid), results for substance P are shown in FIG. 25B (lymph node) and 25E (lymph fluid), and results for vasoactive intestinal peptide are shown in FIG. 25C (lymph node) and 25F (lymph fluid). The results suggest frequencies at which specific neurotransmitters or neuropeptides may be released into the lymph node compartment.

Figure 26:
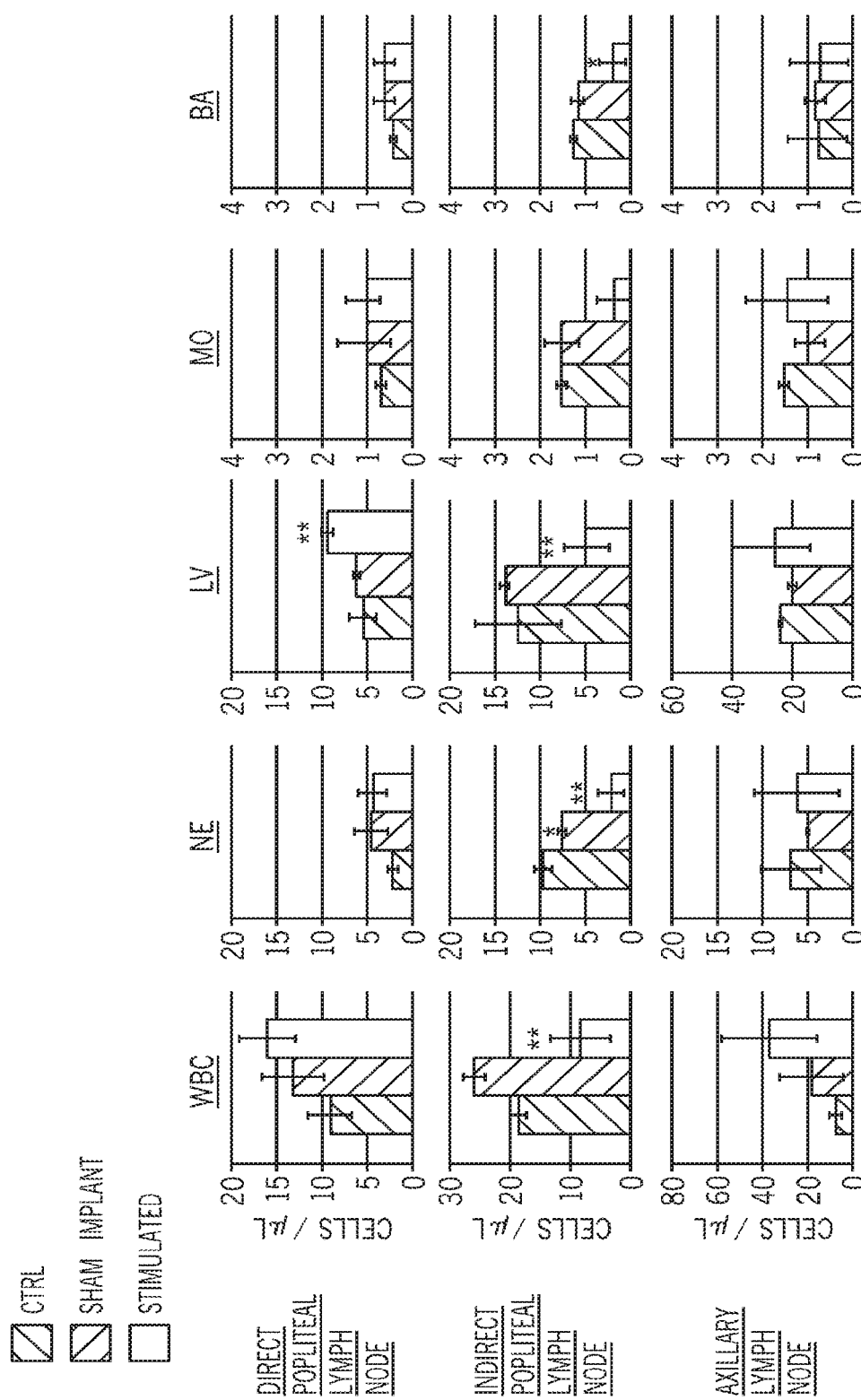
FIG. 26 is a comparison panel showing the number of immune cells within lymph node excised from stimulated, sham, and naïve animals after dissected and dissociation into single cell suspensions.
Figure 27:
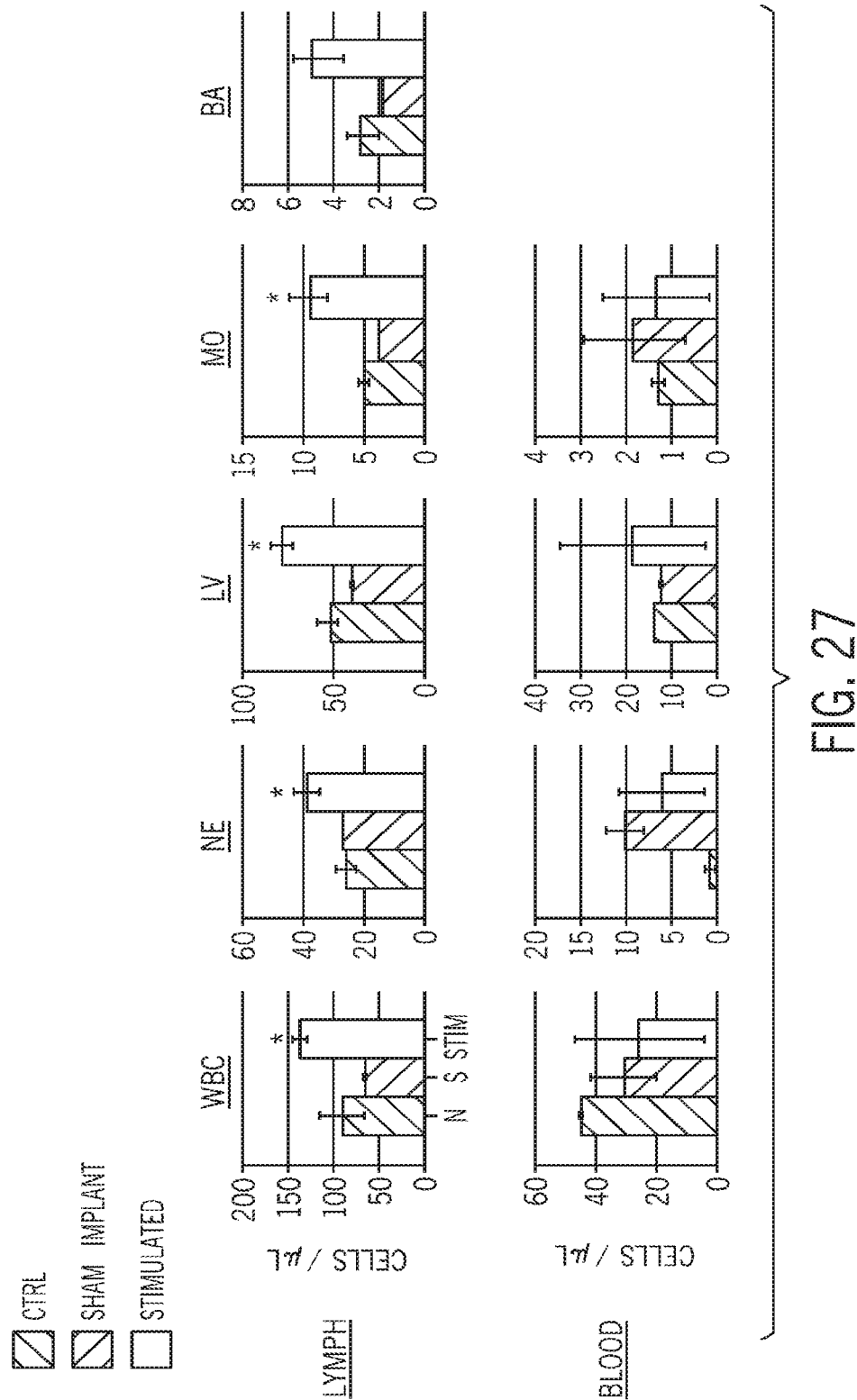
FIG. 27 is a comparison panel showing the number of immune cells per microliter in collected lymphatic fluid or blood for the same subjects as FIG. 26.
Figure 28:
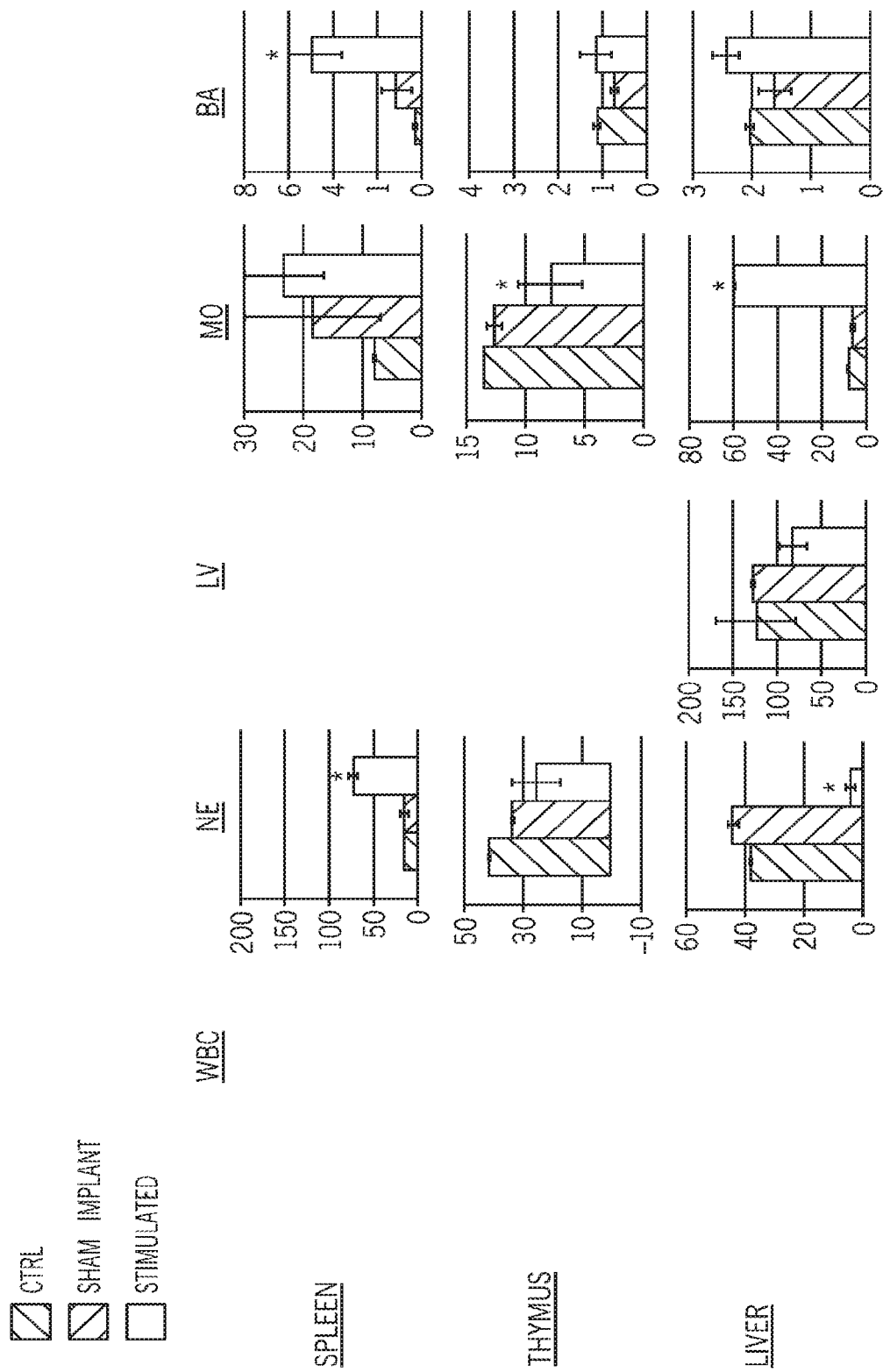
FIG. 28 is a comparison panel showing the number of immune cells/microliter of dissociated sample from various primary immune organs for the same subjects as FIGS. 26 and 27.

In addition to measuring the neurotransmitters and neuropeptides associated with neural stimulation, total cell number within the lymph nodes (and surrounding tissue/organs) where measured as an initial measurement of an adaptive immune function (i.e. immune cell recruitment or trapping in lymph tissue for increased antigen screening). FIG. 26 shows a comparison panel of the results of cell counts from the direct stimulated lymph node, the contralateral ("unstimulated" or indirectly stimulated lymph node), and a distant lymph node (axillary lymph node in the arm) while FIG. 27 shows a comparison panel of the result for cell counts for lymph tissue and blood in the subjects and FIG. 28 shows a comparison panel of results for cell counts in the spleen, thymus, and liver for the subjects. Stimulation parameters for the results shown in FIGS. 26-28 were again 0.5 V at 20 Hz for 5 minutes durations (with a 200 us pulse width). Total white blood cell counts (WBC) were measured along with specific cell counts for neutrophils (NE), lymphocytes (LV), monocytes (MO), and basophils (BA), each subset of the white blood cell populations. For the results shown in FIGS. 26-28, the leftmost bar in all graphs represents naïve control subjects, the middle bar in all graphs represents sham subjects (electrode implantation but no stimulation), and the rightmost bar in all graphs represents stimulated subjects. Lymphocyte numbers were dramatically increased after only five minutes of stimulation within the directly stimulated lymph node, while other cell types were unchanged. This supports lymphocyte-specific mechanisms for trapping or rapidly recruiting lymphocytes within the lymph node via neuromodulation within a short time frame. In addition, antigen presenting cells such as monocytes did not show an increase in cell numbers within the five minutes stimulation period (which suggests that cells found primarily within surrounding tissue and not in blood either do not respond to stimulation induced recruitment or required a longer stimulation/experiment time for response). In contrast, a completely opposite effect was observed within contralateral (or indirectly stimulated lymph node). That is, numbers of all blood cell sub-types were dramatically decreased within that opposite lymph node. It is interesting to note that catecholamine and neuropeptide levels where not dramatically different in the direct and indirectly stimulated lymph node. However, the method of measuring concentrations within the entire lymph node does not take in account differential changes in local concentrations (i.e. around nerve endings innervating specific lymph node regions or compartments). In the distant axillary lymph node there was no statistical change in the numbers of any cell type between the stimulate subjects and controls. This suggests that systemic or global changes in neurotransmitter/neuropeptide levels are not responsible for the differential modulation of immune cell migration/recruitment (i.e. adaptive immune function) in the two popliteal nodes. This initial data is indicative of a crossed neural reflex as depicted in FIG. 4.

In addition, cell numbers within the lymphatic fluid were dramatically increased (despite the increase in lymphocyte numbers in the direct stimulated lymph node). This suggests that the contralateral or indirect effect of neuromodulation of the adaptive immune reflex generated an opposing response across a number of nodes in the lymphatic system, causing an opposite "release" of immune cells from a number of neighboring nodes (in contrast to the recruitment into the locally stimulated node). However, again this effect was not shown to reach the blood compartment within the five minutes stimulation time point.

FIG. 28 shows that the neural network and signaling may have extended to other primary immune tissues/organs, as specific cell types were either recruited or released from the liver, spleen, and thymus. Interestingly, monocytes seemed to be preferentially trapped within the liver due to stimulation of the adaptive immune reflex, neutrophils and basophils appeared to be recruited preferentially to the spleen, while lymphocytes were also released by the liver back in circulation. This again shows differential modulation of different parts of the adaptive immune systems (i.e. antigen presentation versus cognate antigen screening), and between the adaptive and innate immune systems and cell types.

Figure 29:
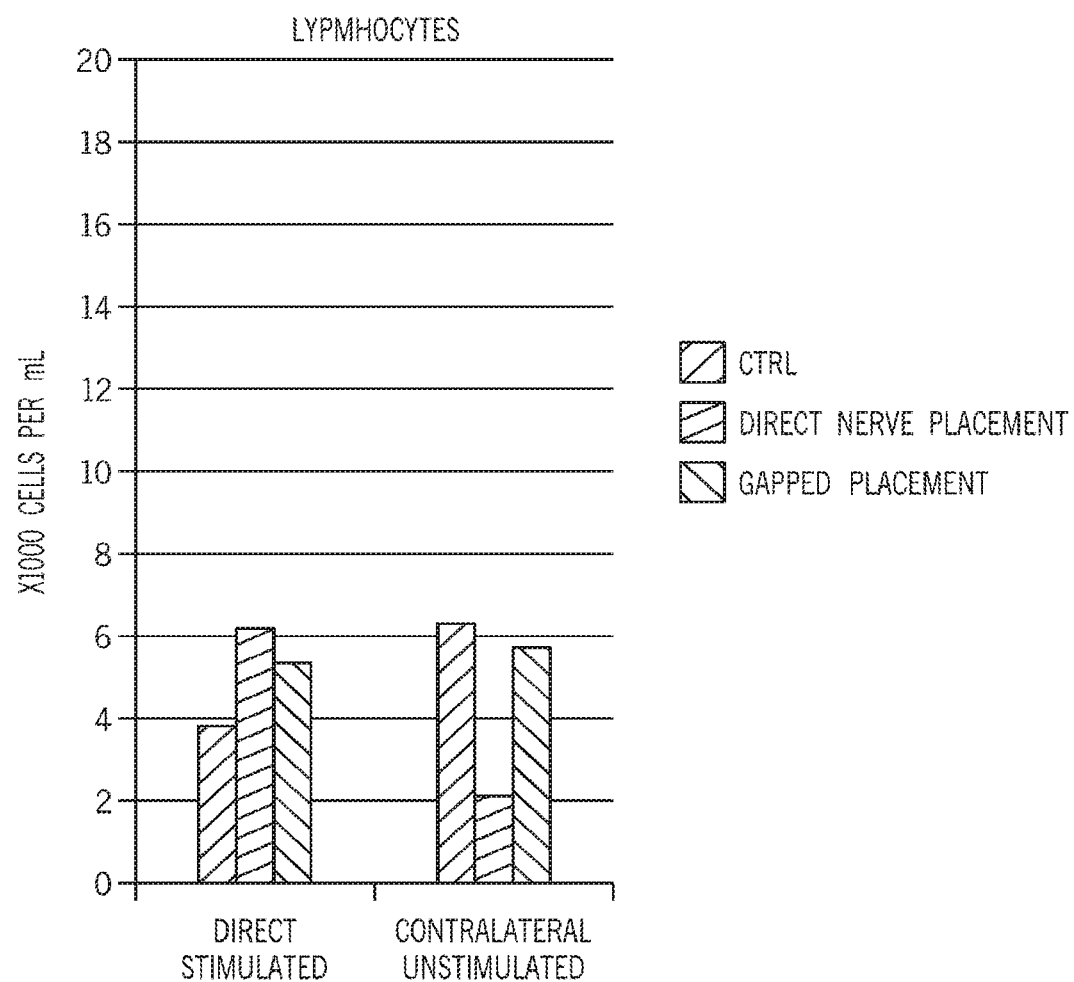
FIG. 29 shows simulation results of differential stimulation based on electrode placement in which a gap between the electrode and the nerve results in firing of only a subset of axons.

FIG. 29 shows results of partial firing or full firing of axons based on electrode placement. The leftmost bars in the direct and contralateral datasets represent control, the middle bars represent normal electrode placement directly on the nerve, and the rightmost bars represent gapped or more distant (relative to direct contact) electrode placement. In the experiments, electrodes were placed via insertion through small incision in the skin (instead of full surgical exposure of the nerve for placement). In one experiment, the electrode was inserted across the nerve (similar to full surgical placement). In another experiment, the electrode was place on one side of the nerve (with an additional gap between the electrode and nerve). A control was run as with previous experiments. Using the same stimulation parameters as the previous experiments (i.e. 0.5 V, 20 Hz, 200 us pulse width), the electrode placed across the nerve resulted in the expected response (i.e. increase in number of cells in the directly stimulation lymph node and decrease in the contralateral). However, when the electrode was placed with an additional gap between the electrode and nerve, the direct but not contralateral response was observed. This is evidence that the neural pathways providing control over the direct and contralateral response (e.g. efferent and afferent neural pathways) may enable differential control of immune function across the body. In this case, an electrode across (and directly against) the nerve fires all axons within the nerve bundle, but an electrode placed on one side (and with a gap) may fire only a portion/sub-set of those axons.

Figure 30:
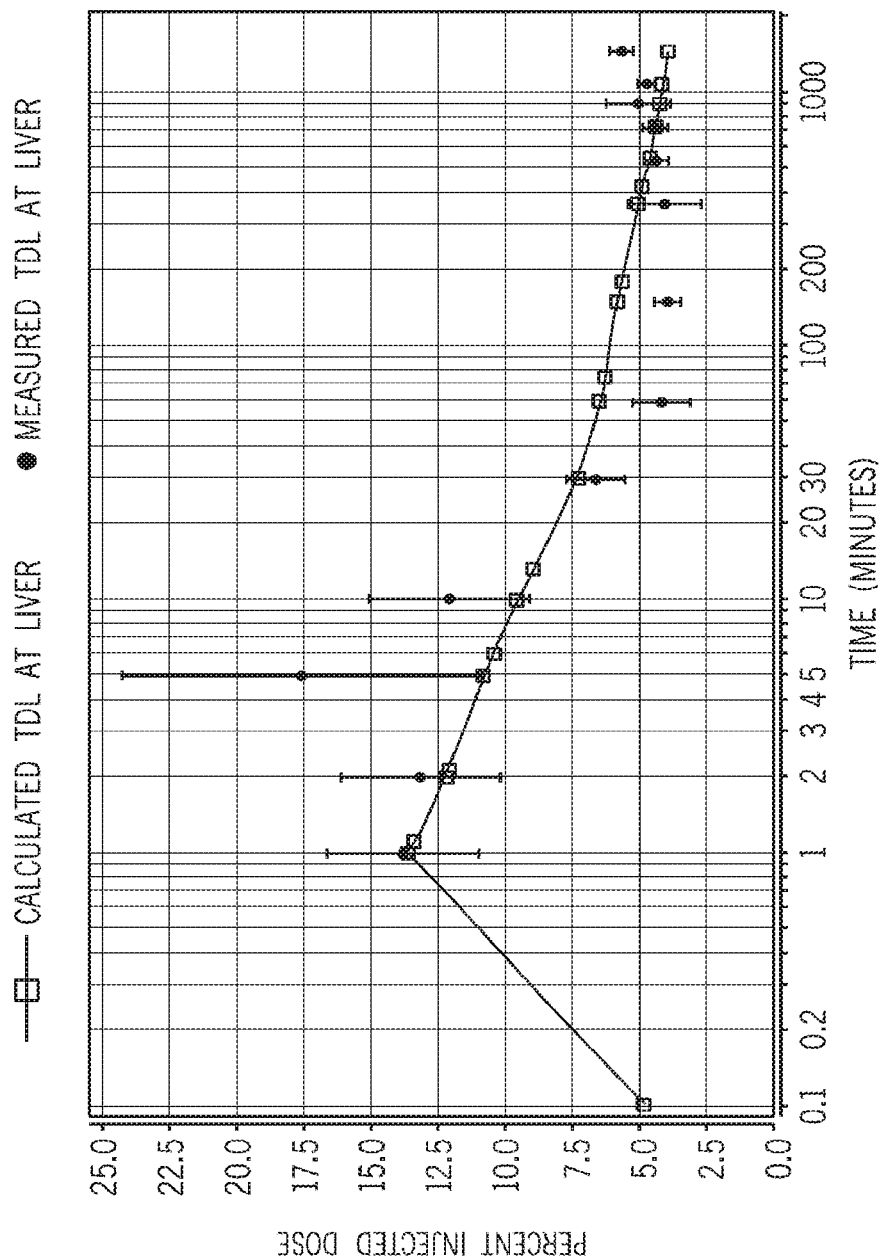
FIG. 30 shows simulated and experimental results for lymphocyte uptake in the liver for the same subject/experiment in FIG. 29.
Figure 31:
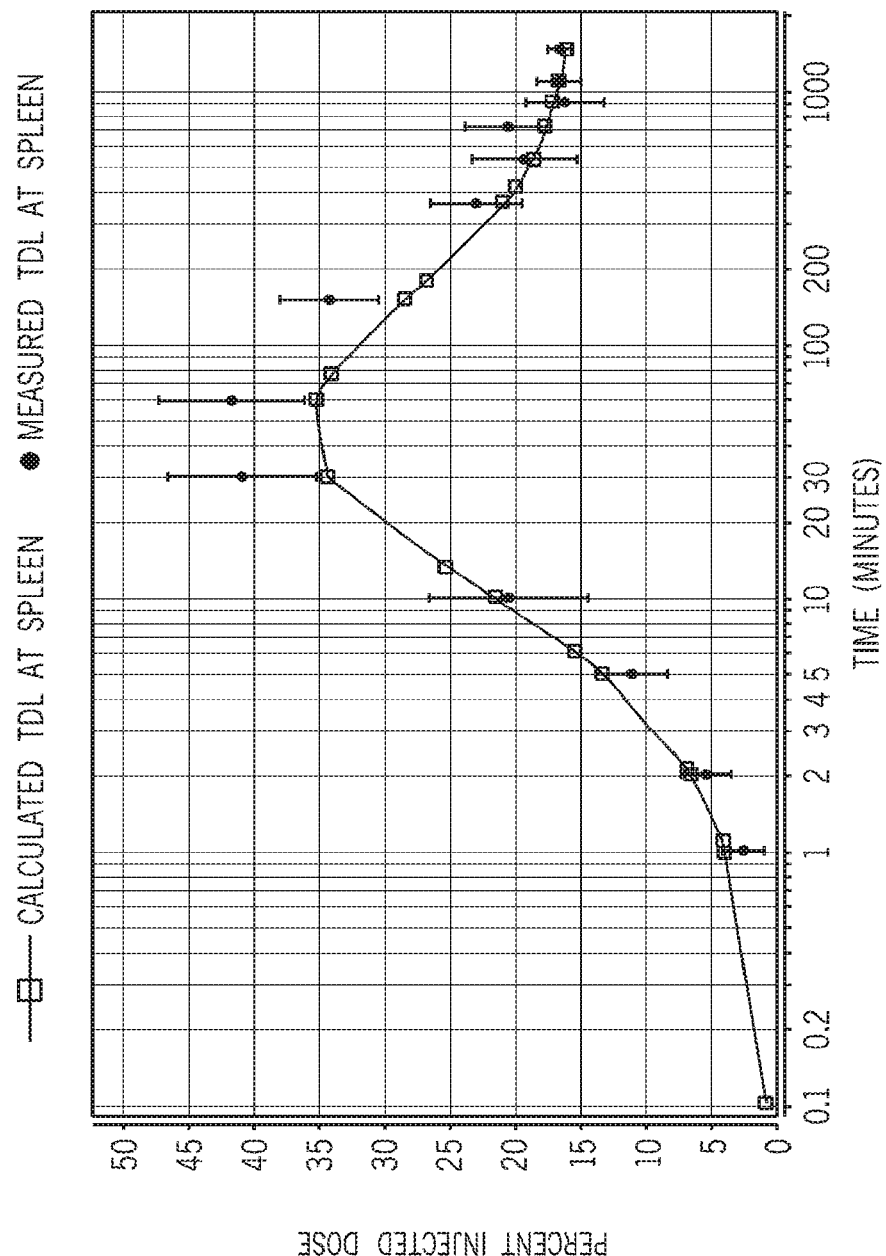
FIG. 31 shows simulated and experiment results for lymphocyte uptake in the spleen for the same subject/experiment in FIG. 29.

FIGS. 30 and 31 show that both liver and spleen are also expected to recruit (not "expel") lymphocytes as shown in the neuromodulation data as provided herein. That is, the demonstrated egress of lymphocytes from the liver and spleen as provided herein is an unexpected result based on previously-published data. The liver and spleen lymphocyte egress mediated as a response to neuromodulation as shown herein may be the result of long-loop reflex (like that shown in FIG. 9) inhibiting an effect in the contralateral lymph node or the failure of the traditional antigen injection to mimic the neurological inputs necessary for triggering the adaptive immune reflex.

Figure 32:
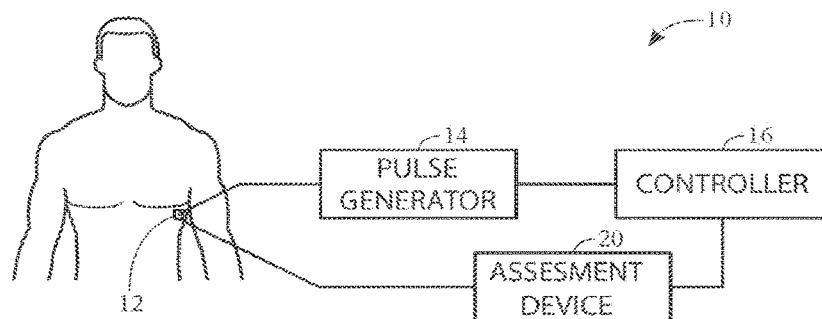
FIG. 32 a schematic representation of a neuromodulation system using an electrode positioned on a nerve according to embodiments of the disclosure.

The disclosed neuromodulation techniques may be used in conjunction with a neuromodulation system. FIG. 32 is a schematic representation of a system 10 for neuromodulation, such as stimulation of nerves innervating lymphatic tissue. The depicted system includes an implanted electrode assembly 12 coupled to a pulse generator 14 via or more leads. The electrode assembly 12 is configured to receive energy pulses via the leads, which in turn result in a clinical effect at the site of electrode placement. In certain embodiments, the pulse generator 14 may be implanted at a biocompatible site (e.g., the abdomen), and the lead or leads couple the electrode assembly 12 and the pulse generator 14 internally. In certain embodiments, the electrode assembly 12 and/or the pulse generator 14 may communicate wirelessly, for example with a controller 16 that may in turn provide instructions to the pulse generator 14. In other embodiments, the pulse generator 14 may be an external device, e.g., may operate to apply energy transdermally or in a noninvasive manner, and may, in certain embodiments, be integrated within the controller 16. In embodiments in which the pulse generator 14 is implanted, the implantation site may be selected to reduce tension via the lead or leads. Once positioned to apply energy pulses to the desired site, the system 10 may initiate neuromodulation to achieve desired clinical effects. The stimulation includes stimulation of at least one neuron innervating the lymphatic tissue. The stimulation may include stimulation of sensory and/or efferent/effector nerve fibers.

In certain embodiments, the system 10 may include an assessment device 20 that is coupled to the controller 16 and that assesses proxy characteristics that are indicative of whether the modulation goals have been achieved. For example, the modulation may result in local lymphatic tissue or function changes, such as tissue structure changes, increased drainage, etc. The modulation may also result in immune function changes, such as a change in a population of immune cells in a change in a presence or concentration of chemical compounds by the lymphatic tissue. Based on the assessment, the modulation parameters of the controller 16 may be altered. For example, if a successful modulation is associated with an increase in lymph node size, then a lack of observation of the size increase within a defined time window relative to the start of the procedure (e.g., 5 minutes, 30 minutes), may require an increase in the frequency or voltage or other parameters, which in turn may be provided by an operator to the controller 16 for defining the energy pulses of the pulse generator 14.

Figure 33:
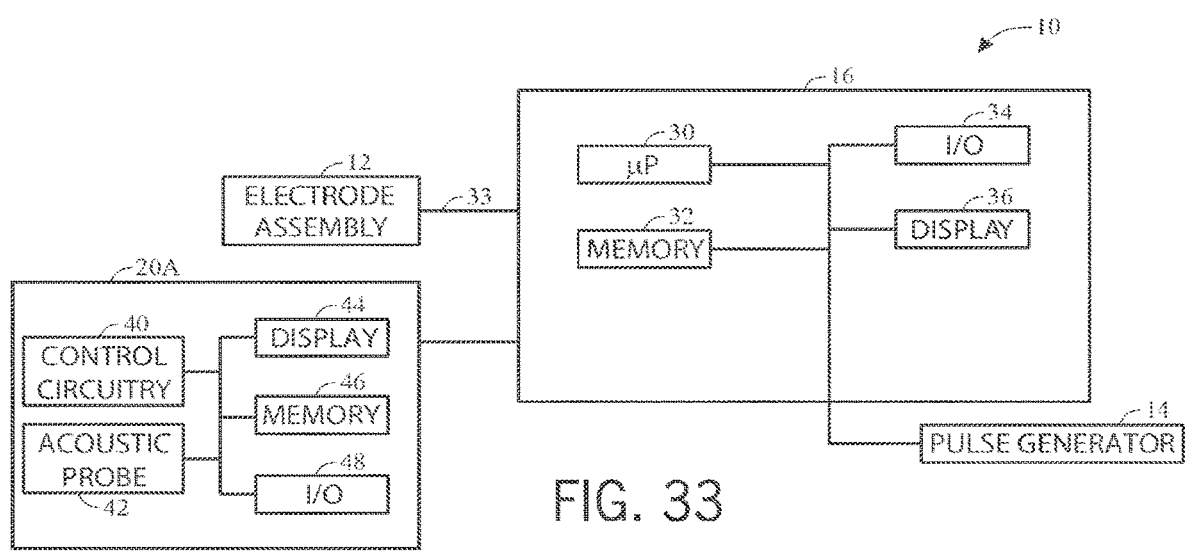
FIG. 33 is a block diagram of the system of FIG. 32 according to embodiments of the disclosure.

FIG. 33 is a block diagram of certain components of the system 10. As provided herein, the system 10 for neuromodulation may include a pulse generator 14 that is adapted to generate energy pulses for application to a tissue or nerve of a subject. The pulse generator 14 may be implantable or may be integrated into an external device, such as a controller 16. The controller 16 includes a processor 30 for controlling the system 10 Software code or instructions are stored in memory 32 of the controller 16 for execution by the processor 30 to control the various components of the device. The controller 16 and/or the pulse generator 14 may be connected to the electrode assembly 12 via one or more leads 33.

The controller 16 also includes a user interface with input/output circuitry 34 and a display 36 that are adapted to allow a clinician to provide selection inputs or stimulation parameters to or more stimulation programs to treat and/or monitor the subject's disorder(s). Each stimulation program may include one or more sets of stimulation parameters including pulse amplitude, pulse width, pulse frequency, etc. The pulse generator 14 modifies its internal parameters in response to the control signals from controller device 16 to vary the stimulation characteristics of energy pulses transmitted through lead 33 to the subject. Any suitable type of pulse generating circuitry may be employed including constant current, constant voltage, multiple-independent current or voltage sources, etc. The energy applied is a function of the current amplitude and pulse width duration.

In one embodiment, the memory 32 stores different operating modes that are selectable by the operator. For example, the stored operating modes may include instructions for executing a set of stimulation parameters associated with a particular treatment and/or monitoring site. Different sites may have different associated stimulation parameters. Rather than having the operator manually input the modes, the controller 16 may be configured to execute the appropriate instruction based on the selection. In another embodiment, the memory 32 stores operating modes for different types of treatment and/or monitoring. For example, activation of the lymphatic tissue function may be associated with a different stimulating voltage or frequency range relative to those associated with depressing or blocking nerve output and/or the lymphatic tissue function. In a specific example, the blocking frequencies are in the range of at least 1 kHz while the activating frequencies are less than 1 kHz.

In another embodiment, the memory 32 stores a calibration or setting mode that permits adjustment or modification of the stimulation parameters to achieve a desired result. In one example, the stimulation starts at a lower energy parameter (e.g., 0.5V or 0.5 Hz) and increases incrementally, either automatically or upon receipt of an operator input. In this manner, the operator may observe the stimulation effects as the stimulation parameters are being changed.

The controller 16 may also be configured to receive inputs related to lymphatic function as an input to the selection of the stimulation parameters. For example, when an imaging modality is used to assess lymphatic flow, the controller 16 may be configured to receive a calculated flow value. Based on whether the flow value is above or below a threshold, the stimulation parameters may be modified. In another example, the controller 16 may receive inputs from one or more sensors configured to assess concentration of released molecules as a result of stimulation, e.g., peptides or catecholamines. Based on the sensed concentration, the stimulation parameters may be modified.

In another implementation, a successful stimulation parameter set may also be stored by the controller 16. In this manner, subject-specific parameters may be determined. Further, the effectiveness of such parameters may be assessed over time. If a particular set of parameters is less effective over time, the subject may be developing insensitivity to the activated pathways.

In the depicted example, ultrasound device 20A includes an acoustic probe 42 that is capable of acquiring image data of a lymphatic tissue to assess a change in size. The ultrasound device 20A may include control circuitry for controlling the acoustic probe 42 and analyzing the acquired image data. The ultrasound device 20A may include additional hardware components, such as a display 44, a memory 46, and an input/output device 46. While the depicted example is of an ultrasound imaging device 20A, the assessment device 20 may include other types of imaging devices (e.g., invasive or noninvasive), or other types of imaging technology, such as magnetic resonance imaging. In addition, the assessment device 20 may include noninvasive optical sensors and monitoring devices. In yet another example, the assessment device 20 may be a flow cytometer that receives a sample from the patient before and after modulation and determines if a change in one or more cell populations has occurred as a result of the neuromodulation.

Figure 34:
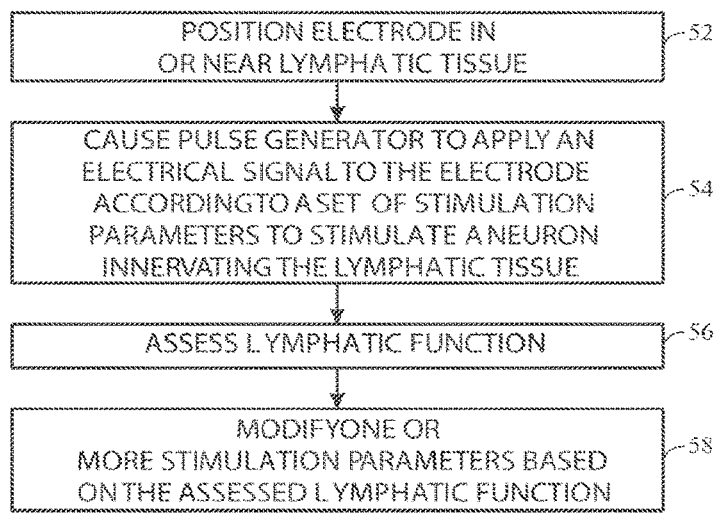
FIG. 34 is a flow diagram of a neuromodulation and monitoring technique according to embodiments of the disclosure.

FIG. 34 is a flow diagram of a method 50 for stimulating immune tissue. In the method, the electrode is positioned on or near a lymphatic tissue or near the nerve of interest at step 52, and the pulse generator applies a plurality of energy pulses to the tissue via the electrode to stimulate the neuron to modulate a lymphatic or immune function of the lymphatic tissue at step 54. Then, the effect of the stimulation is assessed at step 56. For example, one or more direct or indirect assessments of a state of lymphatic or immune function or condition may be used. Based on the lymphatic or immune function as assessed, the modulation parameters of the one or more energy pulses may be modified at step 58 to achieve the desired clinical result. Additionally or alternatively, the function or condition of the stimulated nerve itself may also be used as a metric for determining the effectiveness of the modulation parameters.

The successful modulation may be assessed via a measured clinical outcome, such as an increase in tissue structure size (e.g., lymph node size) or a change in concentration of released molecules e.g., relative to the baseline concentration before the neuromodulation). In one embodiment, a successful modulation may involve an increase in concentration above a threshold, e.g., above a 50%, 100%, 200%, 400%, 1000% increase in concentration relative to baseline. For blocking treatments, the assessment may involve tracking a decrease in concentration of a molecule over time, e.g., at least a 10%, 20%, 30%, 50%, or 75% decrease in the molecule of interest. Further, for certain subjects, the successful blocking treatment may involve keep a relatively steady concentration of a particular molecule in the context of other clinical events that may tend to increase the molecule. That is, successful blocking may block a potential increase. The increase or decrease may be measured within a certain time window from the start of treatment, e.g., within 5 minutes, within 30 minutes. In certain embodiments, if the neuromodulation is determined to be successful, the change in the neuromodulation is an instruction to stop applying energy pulses. In another embodiment, one parameter of the neuromodulation is changed if the neuromodulation is not successful. For example, the change in modulation parameters may be an increase in modulation frequency, such as a stepwise increase in frequency of 10-100 Hz and assessment of the desired characteristic until successful neuromodulation is achieved. In another implementation, the pulse width may be changed. In other embodiments, two or more of the parameters may be changed together. If the neuromodulation is not successful after multiple parameter changes, the position of the electrode may be changed.

In one embodiment, assessments may be performed before and after stimulation to assess a change in lymphatic function as a result of the stimulation. If a desired change in the state of the assessed characteristic of lymphatic function is above or below a threshold, appropriate modification in the modulation parameters may be made. For example, if the change in the characteristic relative to the threshold is associated with successful activation of the lymph tissue, the energy applied during neuromodulation may be stepped back to the minimum level that supports the desired outcome. If the change in the characteristic relative to the threshold is associated with insufficient activation of the lymph tissue, certain modulation parameters, such as the modulation voltage or frequency, the pulse shape, the stimulation pattern, and/or the stimulation location may be changed. It should also be understood that certain desired clinical outcomes may be instead associated with blocking activation. In such embodiments, an assessment of decreased neural and/or lymphatic function is associated with maintaining the modulation parameters, and the modulation parameters may be modified if an undesired level of lymphatic activity persists.

Further, the assessed characteristic or condition may be a value or index (e.g., a flow rate, a concentration, a cell population), which in turn may be analyzed by any suitable technique. For example, a relative change exceeding a threshold may be used to determine if the modulation parameters are modified.

Figure 35:
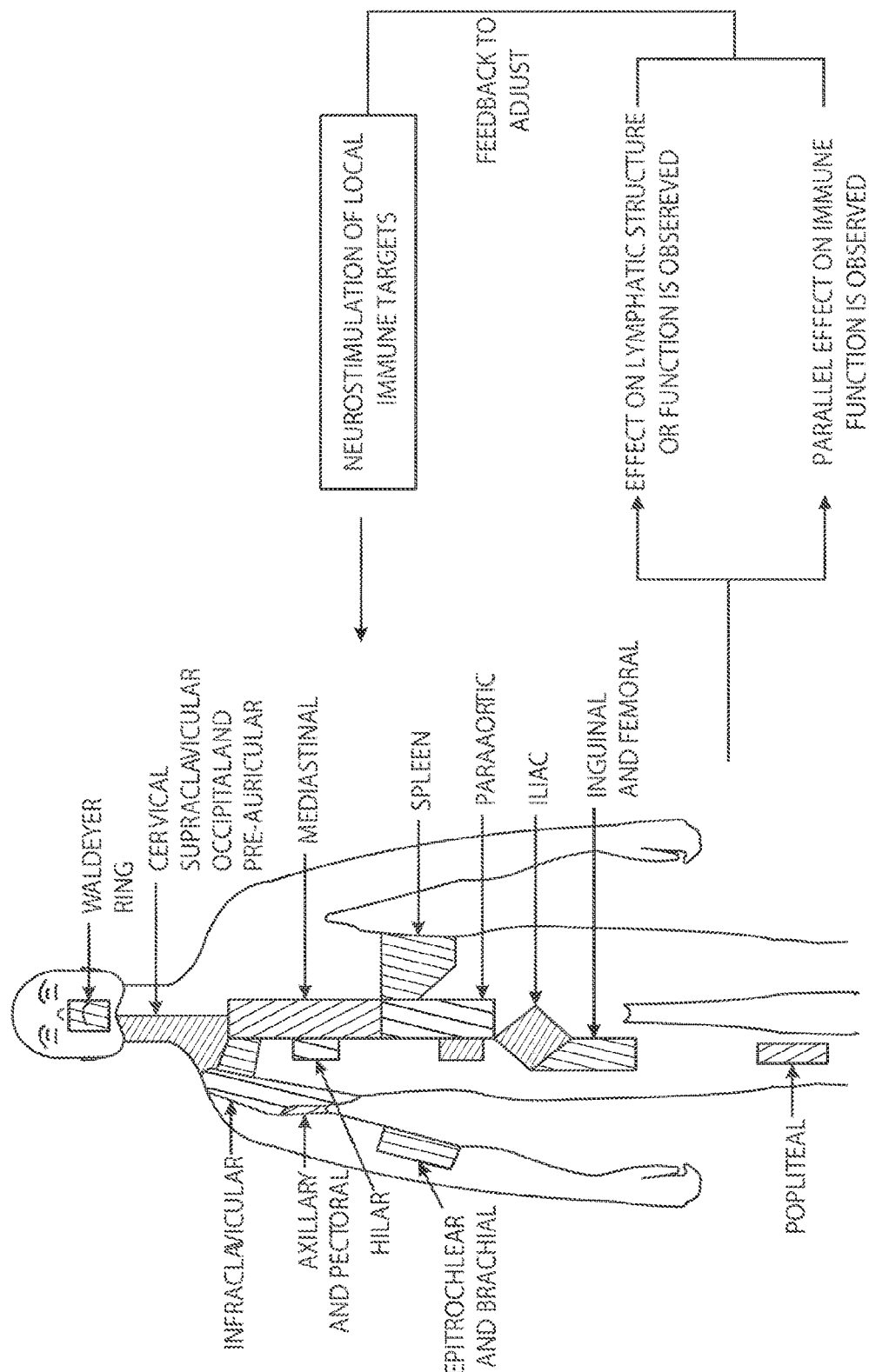
FIG. 35 is a schematic representation of a neuromodulation system for immunomodulation according to embodiments of the disclosure.
Figure 36:
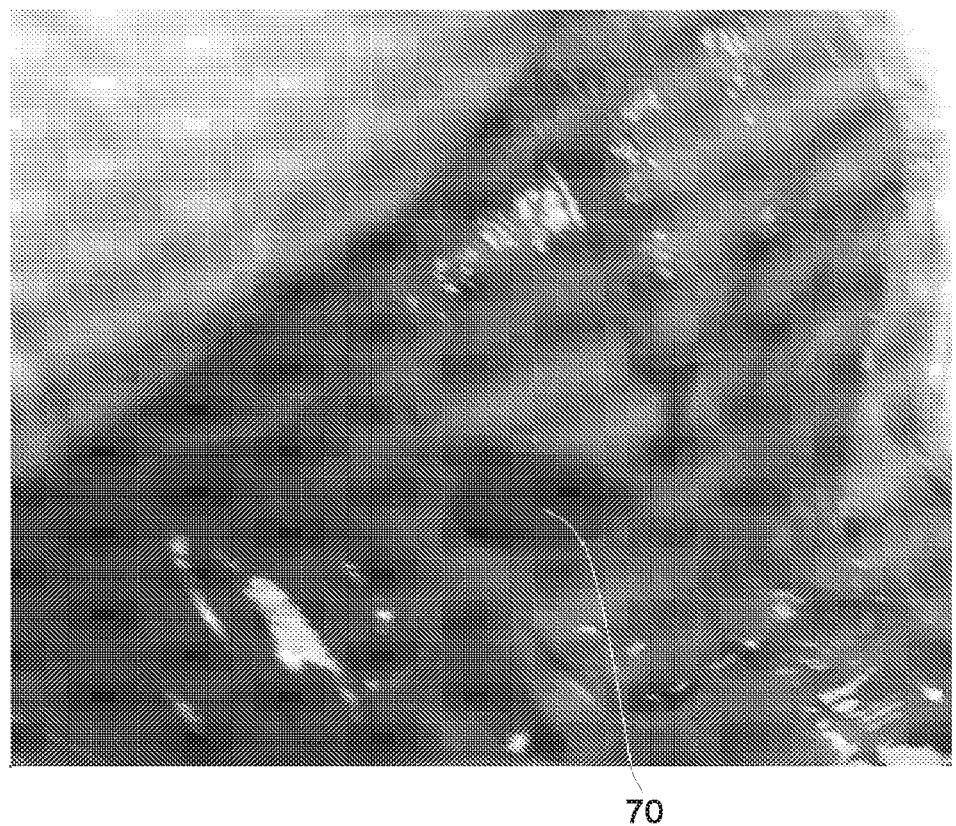
FIG. 36 is an image of a stimulated popliteal lymph node labelled with dye for visualization.

FIG. 35 is an overview of the location of various lymphatic tissues in the body showing effects of neurostimulation of immune structures. The effects, in turn, may be assessed to adjust one or more parameters of the stimulation. As discussed herein, the stimulation may be assessed via one or more assessment techniques. FIG. 36 is an image of a stimulated popliteal lymph node 70 labeled with dye. Such labeling may be used for in vivo size change assessment before, during and/or after modulation.

Figure 37:
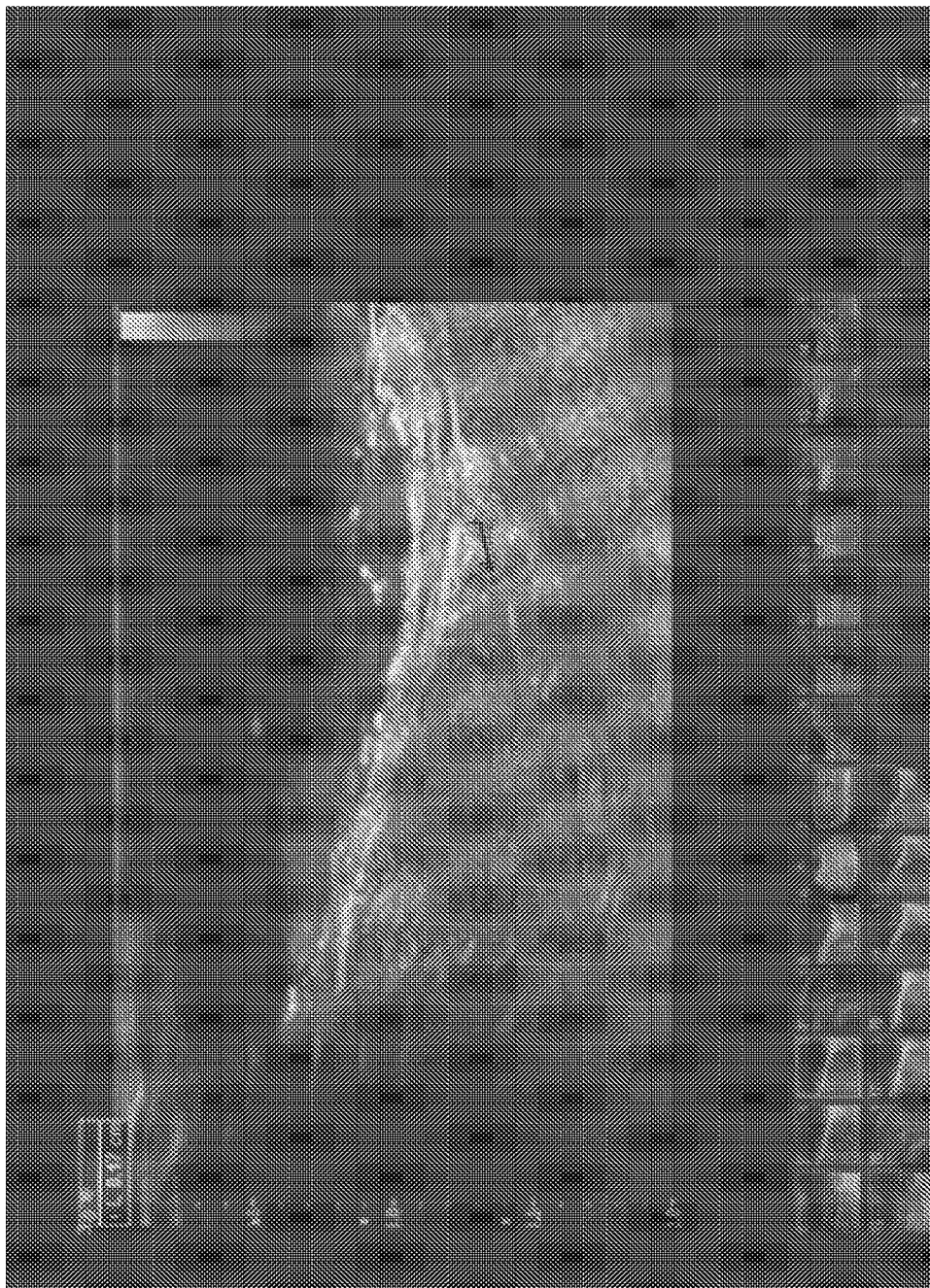
FIG. 37 is an ultrasound image of the stimulated popliteal lymph node before stimulation with an embedded length measurement of the lymph node.
Figure 38:
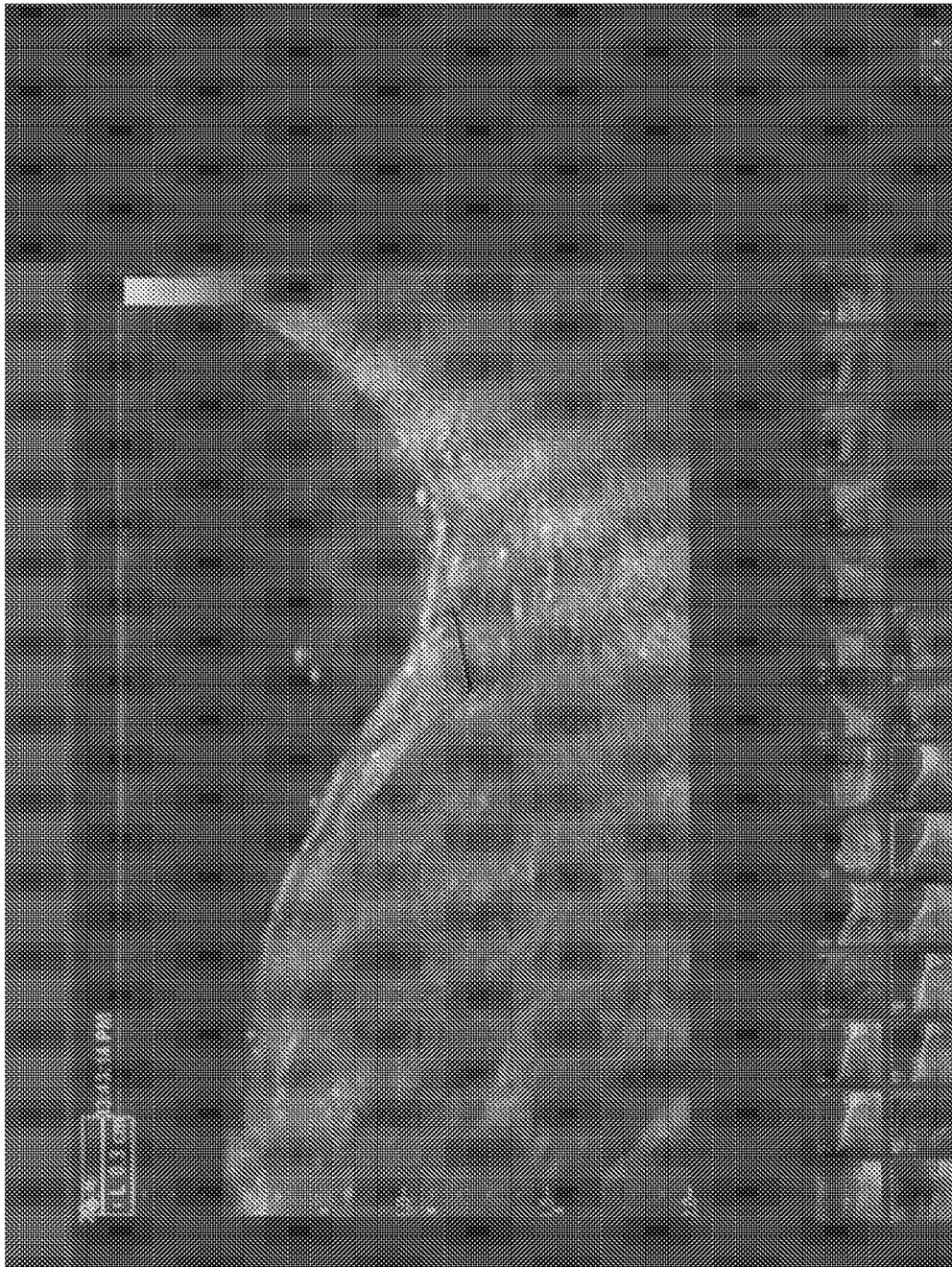
FIG. 38 is an ultrasound image of the stimulated popliteal lymph node after stimulation with an embedded length measurement of the lymph node.

In one embodiment, ultrasound imaging is used to assess the lymph node size. FIG. 37 shows an ultrasound image of the directly stimulated popliteal lymph node of the subject (as described above) before electrode implantation and neuromodulation. The size of the lymph node measured using the ultrasound system interface (0.17 cm) closely matches that of the non-stimulated lymph node resected in FIG. 7. Sizing was performed by outlining the change in ultrasound contrast within the popliteal fat pad associated with the lymphatic structure. FIG. 38 shows an image and measurement of the same popliteal lymph node after the 5 minutes stimulation described above (i.e. 20 Hz, 0.5 V, 200 us); post-stimulation size increased to 0.3 cm. This data demonstrates that the neurotransmitter release responsible for lymphatic and immune modulation has clear and measurable effects on tissue structures that are capable of being monitoring using non-invasive imaging technologies.

Figure 39:
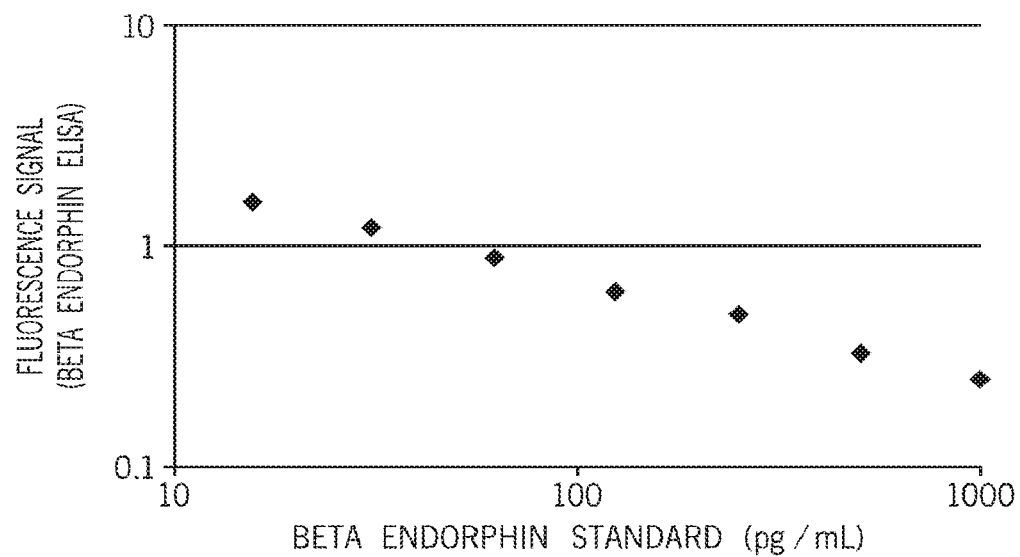
FIG. 39 is a plot of the calibration of a competition assay to fluorescently detect beta endorphin.
Figure 40:
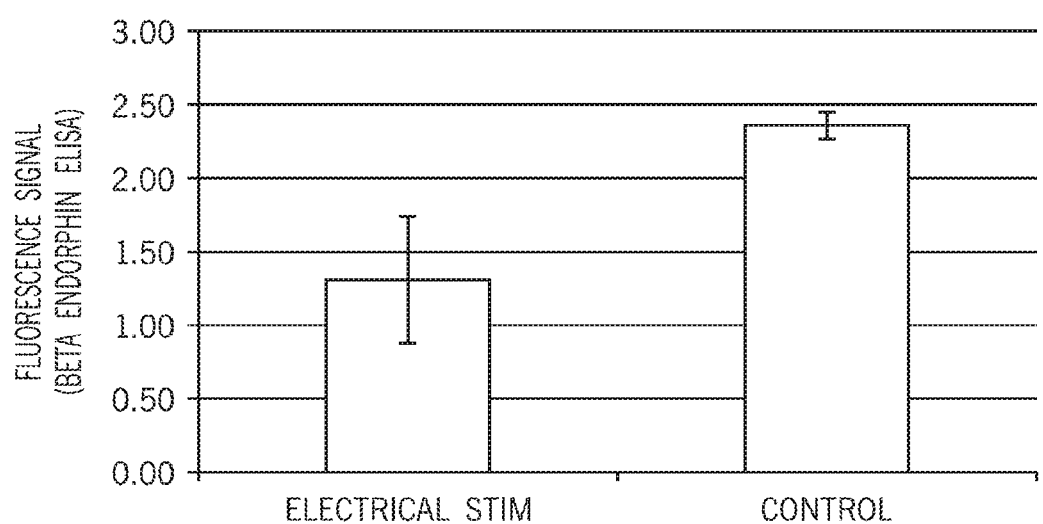
FIG. 40 is a graph showing the results of the assay for a stimulated subject relative to an unstimulated control.

FIG. 39 is a plot of the fluorescence signal associated with a known beta endorphin standard that was used to calibrate experimental results. The plot with of signal intensity (y-axis) vs. concentration of the standard (x-axis) shows results from a competition assay. Accordingly, a lower fluorescence signal is associated with a higher concentration of beta endorphin. FIG. 40 is a graph of results from an animal study showing that lymphatic stimulation drives an increase in beta endorphin as measured in the interstitial fluid of the spleen or blood of the stimulated subject. In one embodiment, stimulation cases a release of beta endorphin from immune cell stores, which in turn is detectable in an interstitial fluid or blood sample. The stimulated sample was associated with a lower fluorescence signal, indicating a higher beta endorphin concentration. Accordingly, assessment of the effectiveness of stimulation may be performed via blood concentration measurements of proxy markers of immune activity, such as beta endorphin. Further, as provided herein, the neuromodulation may be associated with an increase in endogenous opioid concentration and, in turn, pain-relieving therapeutic benefits.

Technical effects of the present disclosure include stimulation of an adaptive immune reflex pathway via neuromodulation to generate a differential local physiological or immunological change. For example, the disclosed techniques permit stimulation of lymphatic tissue that is otherwise challenging to target via systemic techniques, such as drug therapy. In addition, the disclosed techniques may be used to treat subjects with a variety of clinical conditions, including those suffering from lymphatic disorders, cancer patients, patients in need of immunomodulation, etc. The technique may also be utilized as a supportive therapeutic tool. For instance, neuromodulation of lymph tissue and local recruitment of cells may be utilized to localized cells injected into a patient for cell-based therapies (e.g. DC-based cancer immunotherapy), or to limit metastatic spread from a primary tumor during chemotherapy. A more targeted effect on the adaptive immune system may also be achieved by further localization of the neural stimulation signal (i.e. placement of the electrodes closer to the local lymph target), differential excitation of afferent versus efferent components of the neural pathway, and or blocking of the excitatory signal through application of a blocking stimulation (i.e. high frequency stimulation) upstream to the stimulatory electrodes.

The specific embodiments described above have been shown by way of example, and it should be understood that these embodiments may be susceptible to various modifications and alternative forms. It should be further understood that the claims are not intended to be limited to the particular forms disclosed, but rather to cover all modifications, equivalents, and alternatives falling within the spirit and scope of this disclosure.

The invention claimed is:

1. A method of neuromodulation, comprising:
applying one or more energy pulses to a neuron of a subject to deliver sufficient energy to the neuron to neurally modulate a lymphatic tissue in response to applying the one or more energy pulses;
acquiring image data of the lymphatic tissue using an ultrasound imaging probe; and
changing modulation parameters of the one or more energy pulses based on the image data.

2. The method of claim 1, wherein the lymphatic tissue is a lymph node.

3. The method of claim 1, wherein the neuron is a parasympathetic or sympathetic neuron innervating a primary, secondary, or tertiary lymphatic tissue structure or communicating tissue.

4. The method of claim 1, wherein the subject has a diagnosis of an autoimmune disorder.

5. The method of claim 1, wherein acquiring the image data comprising acquiring baseline image data and post-modulation image data.

6. The method of claim 5, wherein the post-modulation image data is acquired within 30 minutes of applying the one or more energy pulses.

7. The method of claim 1, wherein changing the modulation parameters comprises decreasing or stepping back energy levels of the one or more energy pulses.

8. The method of claim 1, wherein the image data is indicative of an increase in size of the lymphatic tissue above a threshold, wherein the increase in size is indicative of successful modulation.

9. The method of claim 1, wherein the increase in size is an increase in volume of the lymphatic tissue.

10. The method of claim 1, wherein the image data is indicative of a lack of change in size of the lymphatic tissue relative to a threshold, and wherein a controller is configured to increase the modulation parameters based on the lack of change in size.

11. The method of claim 1, wherein applying the one or more energy pulses causes the lymphatic tissue to increase in size, wherein the lymphatic tissue is a lymph node, and wherein the increase in size of the lymph node is associated with a decrease in lymphocyte egress from the lymph node.

12. A system for neuromodulation of lymphatic tissue, comprising:
an energy application device configured to apply one or more energy pulses to a neuron of a subject to deliver sufficient energy to the neuron to neurally modulate a lymphatic tissue in response to applying the one or more energy pulses;
a noninvasive ultrasound imaging probe configured to acquire image data of the lymphatic tissue before and after neurally modulating the lymphatic tissue; and
a controller configured to:
cause the energy application device to generate the one or more energy pulses according to modulation parameters;
identify a change in size of the lymphatic tissue caused by applying the one or more energy pulses based on the image data; and
change the modulation parameters based on the identified change in size of the lymphatic tissue.

13. The system of claim 12, wherein the lymphatic tissue is a lymph node.

14. The system of claim 12, wherein the subject has a diagnosis of an autoimmune disorder.

15. The system of claim 12, wherein the change in size is relative to a baseline size determined from the image data acquired before neurally modulating the lymphatic tissue.

* * * * *